United States Patent
Fenton et al.

(10) Patent No.: US 7,211,586 B2
(45) Date of Patent: May 1, 2007

(54) SUBSTITUTED TETRAHYDROISOQUINOLINES

(75) Inventors: Garry Fenton, Brentwood (GB); Neil Victor Harris, Tilbury (GB)

(73) Assignee: Aventis Pharma Limited, West Malling (GB)

( * ) Notice: Subject to any disclaimer, the term of this patent is extended or adjusted under 35 U.S.C. 154(b) by 399 days.

(21) Appl. No.: 10/715,662

(22) Filed: Nov. 18, 2003

(65) Prior Publication Data

US 2004/0122047 A1 Jun. 24, 2004

Related U.S. Application Data

(63) Continuation of application No. PCT/GB02/02517, filed on Jun. 5, 2002.

(60) Provisional application No. 60/311,502, filed on Aug. 10, 2001.

(30) Foreign Application Priority Data

Jun. 6, 2001 (GB) .................................. 0113708.2

(51) Int. Cl.
*A61K 31/4709* (2006.01)
*A61K 31/47* (2006.01)
*C07D 217/12* (2006.01)

(52) U.S. Cl. ..................................... 514/310; 546/146
(58) Field of Classification Search ................ 514/310; 546/146
See application file for complete search history.

(56) References Cited

U.S. PATENT DOCUMENTS 5,236,934 A * 8/1993 VanAtten .................... 514/307
6,608,084 B1 * 8/2003 Bourzat et al. ............. 514/311

OTHER PUBLICATIONS

Boger, et al., Inverse Electron Demand Diels-Alder reactions of 3-Carbomethoxy-2-pyrones. Controlled Introduction of oxygenated Aromatics: Benzene, Phenol, Catechol, Resorcinol, and Pyrogallol Annulation. Regiospecific Total Synthesis of Sendaverine and a Preparation of 6,7-Benzomorphans., J. Org. Chem.; vol. 49; No. 21; 1984; pp. 4033-4044.

\* cited by examiner

*Primary Examiner*—Kamal A. Saeed
(74) *Attorney, Agent, or Firm*—Ronald G. Ori

(57) ABSTRACT

The invention is directed to physiologically active compounds of formula (I):

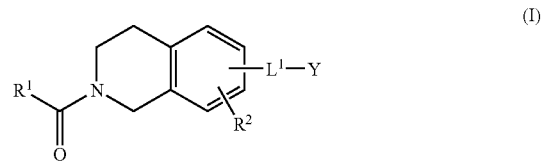

wherein:
$R^1$ represents optionally substituted aryl, optionally substituted heteroaryl, $R^3NH-Ar^1-L^2-$ or $R^3-NH-C(=O)-NH-Ar^2-L^2-$; $R^3$ represents aryl or heteroaryl; $Ar^1$ represents a saturated, partially saturated or fully unsaturated 8- to 10-membered bicyclic ring system containing at least one heteroatom selected from O, S or N; $Ar^2$ represents aryldiyl or heteroaryldiyl; $L^1$ represents a linkage, such as an alkylene linkage; $L^2$ represents an alkylene chain linkage; $R^2$ represents hydrogen, halogen, $C_{1-4}$alkyl or $C_{1-4}$alkoxy; and Y is carboxy or an acid bioisostere;
but excluding compounds where an oxygen, nitrogen or sulfur atom is attached directly to a carbon carbon multiple bond of an alkenylene or alkynylene residue;
and the corresponding N-oxides and ester prodrugs thereof, and the pharmaceutically acceptable salts and solvates of such compounds, and the N-oxides and ester prodrugs thereof.

Such compounds have valuable pharmaceutical properties, in particular the ability to regulate the interaction of VCAM-1 and fibronectin with the integrin VLA-4 (α4β1).

22 Claims, No Drawings

SUBSTITUTED TETRAHYDROISOQUINOLINES

CROSS-REFERENCE TO RELATED APPLICATIONS

This application is a continuation of PCT/GB02/02517, filed Jun. 5, 2002, which claims priority from GB Application No. 0113708.2, filed Jun. 6, 2001, and U.S. Provisional Application No. 60/311,502, filed Aug. 10, 2001; all of these applications incorporated herein by reference.

BACKGROUND OF THE INVENTION

This invention is directed to tetrahydroisoquinoline derivatives, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extracellular matrix interactions are mediated by protein ligands (e.g., fibronectin, VCAM-1 and vitronectin) and their integrin receptors [e.g., $\alpha5\beta1$ (VLA-5), $\alpha4\beta1$ (VLA-4) and $\alpha V\beta3$]. Recent studies have shown these interactions to play an important part in many physiological (e.g., embryonic development and wound healing) and pathological conditions (e.g., tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called $\alpha$ and $\beta$. There are at least fifteen different $\alpha$-subunits ($\alpha1$–$\alpha9$, $\alpha$-L, $\alpha$-M, $\alpha$-X, $\alpha$-IIb, $\alpha$-V and $\alpha$-E) and at least seven different $\beta$ ($\beta1$–$\beta7$) subunits. The integrin family can be subdivided into classes based on the $\beta$ subunits, which can be associated with one or more $\alpha$-subunits. The most widely distributed integrins belong to the $\beta1$ class, also known as the very late antigens (VLA). The second class of integrins are leukocyte specific receptors and consist of one of three $\alpha$-subunits ($\alpha$-L, $\alpha$-M or $\alpha$-X) complexed with the $\beta2$ protein. The cytoadhesins $\alpha$-IIb$\beta3$ and $\beta$-V$\beta3$, constitute the third class of integrins.

The present invention principally relates to agents which modulate the interaction of the ligand VCAM-1 with its integrin receptor $\alpha4\beta1$ (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin $\alpha4\beta1$ mediates both cell-cell and cell-matrix interactions. Cells expressing $\alpha4\beta1$ bind to the carboxy-terminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-$\gamma$, TNF-$\alpha$, IL-1$\beta$ and IL4.

Regulation of $\alpha4\beta1$ mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which $\alpha4\beta1$ binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J. Clin. Invest., 1994, 94, pages 655–662). In the oxazalone-sensitised model of inflammation (contact hypersensitivity response) in mice, intravenous administration of anti-$\alpha4$ specific monoclonal antibodies significantly inhibited (50–60% reduction in the ear swelling response) the efferent response (P. L. Chisholm et al. J. Immunol., 1993, 23, pages 682–688). In a sheep model of allergic bronchoconstriction, HP1/2, an anti-$\alpha4$ monoclonal antibody given intravenously or by aerosol, blocked the late response and the development of airway hyperresponsiveness (W. M. Abraham et al. J. Clin. Invest., 1994, 93 pages 776–787).

SUMMARY OF THE INVENTION

We have now found a novel group of tetrahydroisoquinolines which have valuable pharmaceutical properties, in particular the ability to regulate the interaction of VCAM-1 and fibronectin with the integrin VLA-4 ($\alpha4\beta1$).

Thus, in one aspect, the present invention is directed to aza-bicycles of general formula (I):

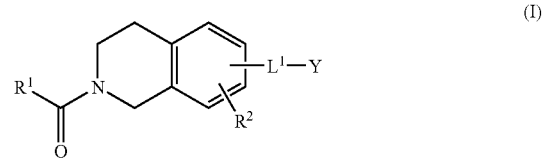

wherein:
$R^1$ represents optionally substituted aryl, optionally substituted heteroaryl, $R^3NH$—$Ar^1$—$L^2$— or $R^3$—NH—C(=O)—NH—$Ar^2$—$L^2$—;
$R^2$ represents hydrogen, halogen, $C_{1-4}$alkyl or $C_{1-4}$alkoxy;
$R^3$ represents optionally substituted aryl or optionally substituted heteroaryl;
$R^4$ is alkyl, aryl, cycloalkyl, heteroaryl or heterocycloalkyl, or alkyl substituted by aryl, an acidic functional group, cycloalkyl, heteroaryl, heterocycloalkyl, —S(O)$_m$R$^5$, —C(=O)—NY$^3$Y$^4$ or —NY$^3$Y$^4$;
$R^5$ represents alkyl, alkenyl, alkynyl, aryl, arylalkyl, arylalkenyl, arylalkynyl, cycloalkyl, cycloalkylalkyl, cycloalkylalkenyl, cycloalkylalkynyl, cycloalkenyl, cycloalkenylalkyl, heteroaryl, heteroarylalkyl, heteroarylalkenyl, heteroarylalkynyl, heterocycloalkyl or heterocycloalkylalkyl;

$R^6$ is hydrogen, alkyl, aryl, arylalkyl, cycloalkyl, cycloalkylalkyl, heteroaryl, heteroarylalkyl, heterocycloalkyl or heterocycloalkylalkyl;

$R^7$ is hydrogen, $R^5$ or alkyl substituted with alkoxy, cycloalkyl, hydroxy, mercapto, alkylthio or —$NY^3Y^4$;

$R^8$ is hydrogen or $C_{1-4}$alkyl;

$R^9$ and $R^{11}$ are each independently selected from hydrogen or a group consisting of amino acid side chains, an acidic functional group, $R^5$, —C(=O)—$R^5$, or —C(=O)—$NY^3Y^4$, or alkyl substituted by an acidic functional group or by $R^5$, —$NY^3Y^4$, —NH—C(=O)—$R^5$, —C(=O)—$R^{12}$—$NH_2$, —C(=O)—$Ar^2$—$NH_2$, —C(=O)—$R^{12}$—$CO_2H$, or —C(=O)—$NY^3Y^4$;

or $R^7$ and $R^9$ together with the atoms to which they attached form a 3- to 6-membered heterocycloalkyl ring;

$R^{10}$ represents $C_{1-6}$alkylene, optionally substituted by $R^4$;

$R^{12}$ is an alkylene chain, an alkenylene chain, or an alkynylene chain;

$R^{13}$ is alkyl, aryl, arylalkyl, cycloalkyl, cycloalkylalkyl, heteroaryl, heteroarylalkyl, heterocycloalkyl or heterocycloalkylalkyl;

$Ar^1$ represents a saturated, partially saturated or fully unsaturated 8 to 10 membered bicyclic ring system containing at least one heteroatom selected from O, S or N, optionally substituted by one or more aryl group substituents;

$Ar^2$ represents aryldiyl or heteroaryldiyl;

$L^1$ represents
  (i) an alkenylene, alkylene or alkynylene linkage each optionally substituted by (a) an acidic functional group, cyano, oxo, —$S(O)_mR^4$, $R^5$, —C(=O)—$R^5$, —C(=O)—$OR^5$, —$N(R^6)$—C(=O)—$R^4$, —$N(R^6)$—C(=O)—$OR^4$, —$N(R^6)$—$SO_2$—$R^4$, —$NY^3Y^4$ or —[C(=O)—$N(R^7)$—$C(R^8)(R^9)]_p$—C(=O)—$NY^3Y^4$, or by (b) alkyl substituted by an acidic functional group, or by $S(O)_mR^4$, —C(=O)—$NY^3Y^4$ or —$NY^3Y^4$;
  (ii) a —[C(=O)—$N(R^7)$—$C(R^8)(R^9)]_p$— linkage;
  (iii) a —$Z^1$—$R^{10}$— linkage;
  (iv) a —$R^{10}$—$Z^1$—$R^{10}$— linkage;
  (v) a —$C(R^8)(R^{11})$—[C(=O)—$N(R^7)$—$C(R^8)(R^9)]_p$— linkage; or
  (vi) a —$L^3$—$L^4$—$L^5$— linkage;

$L^2$ represents an alkylene chain;

$L^3$ and $L^5$ each independently represent a direct bond or an alkylene chain;

$L^4$ represents a cycloalkylene or heterocycloalkylene linkage;

$Y^1$ and $Y^2$ are independently hydrogen, alkenyl, alkyl, aryl, arylalkyl, cycloalkyl, heteroaryl or heteroarylalkyl; or the group —$NY^1Y^2$ may form a cyclic amine;

$Y^3$ and $Y^4$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —$NY^1Y^2$, or one or more —$CO_2R^6$ or —C(=O)—$NY^1Y^2$ groups; or the group —$NY^3Y^4$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof), $R^7$; (ii) may also contain a further heteroatom selected from O, S, $SO_2$, or $NY^5$; and (iii) may also be fused to additional aryl, heteroaryl, heterocycloalkyl or cycloalkyl rings to form a bicyclic or tricyclic ring system;

$Y^5$ is hydrogen, alkyl, aryl, arylalkyl, —C(=O)—$R^{13}$, —C(=O)—$OR^{13}$ or —$SO_2R^{13}$;

$Z^1$ is O, $S(O)_n$, $NR^8$, $SO_2NR^8$, C(=O)$NR^8$ or C(=O);

Y is carboxy or an acid bioisostere;

m is an integer 1 or 2;

n is zero or an integer 1 or 2; and p is zero or an integer 1 to 4;

but excluding compounds where an oxygen, nitrogen or sulfur atom is attached directly to a carbon carbon multiple bond of an alkenylene or alkynylene residue;

and the corresponding N-oxides, and their prodrugs; and pharmaceutically acceptable salts and solvates of such compounds and their N-oxides and prodrugs.

DETAILED DESCRIPTION

In the present specification, the term "compounds of the invention", and equivalent expressions, are meant to embrace compounds of general formula (I) as hereinbefore described, which expression includes the prodrugs, protected derivatives of compounds of formula (I) containing one or more acidic functional groups and/or amino-acid side chains, the pharmaceutically acceptable salts, and the solvates, e.g., hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, p 283 "Bioisosterism In Drug Design"; Yun, Hwahak Sekye, 1993, 33, p 576–579 "Application Of Bioisosterism To New Drug Design"; Zhao, Huaxue Tongbao, 1995, p 34–38 "Bioisosteric Replacement And Development Of Lead Compounds In Drug Design"; Graham, Theochem, 1995, 343, p105–109 "Theoretical Studies Applied To Drug Design:ab initio Electronic Distributions In Bioisosteres"). Examples of suitable acid bioisosteres include: —C(=O)—NHOH, —C(=O)—$CH_2OH$, —C(=O)—$CH_2SH$, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "corresponding protected derivatives" are those where the acidic hydrogen atom has been replaced with a suitable protecting group. For suitable protecting groups see T. W. Greene and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups (i.e., —$CO_2R^{13}$), ethers of hydroxy groups (i.e., —OR$^{13}$), thioethers of mercapto groups (i.e., —SR$^{13}$), and N-benzyl derivatives of imidazoles.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and; dodecyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkyl-O— group in which the alkyl group is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-SO$_2$— group in which the alkyl group is as previously described. Preferred alkylsulfonyl groups are those in which the alkyl group is $C_{1-4}$alkyl.

"Alkylsulfonylcarbamoyl" means an alkyl-SO$_2$—NH—C(=O)— group in which the alkyl group is as previously described. Preferred alkylsulfonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Exemplary alkynylene radicals include ethynylene and propynylene.

"Amino acid side chains" means the substituent found on the carbon between the amino and carboxy groups in α-amino acids. For examples of "corresponding protected-derivatives" of amino acid side chains, see T. W. Greene and P. G. M. Wuts in "Protective Groups in Organic Chemistry" John Wiley and Sons, 1991.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyloxy, heteroaroylamino, heteroaryloxy, hydroxy, nitro, trifluoromethyl, $Y^1Y^2N$—, $Y^1Y^2NCO$—, $Y^1Y^2NSO_2$—, $Y^1Y^2N$—$C_{2-6}$alkylene-$Z^2$— {where $Z^2$ is O, NR$^8$ or S(O)$_n$}, alkylC(=O)—$Y^1N$—, alkylSO$_2$—$Y^1N$— or alkyl optionally substituted with aryl, heteroaryl, hydroxy, or $Y^1Y^2N$—.

"Arylalkenyl" means an aryl-alkenyl- group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O-CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl- group in which the aryl and alkynyl are as previously described. Exemplary arylalkynyl groups include phenylethynyl and 3-phenylbut-2-ynyl.

"Aryldiyl" means an optionally substituted bivalent radical derived from an aryl group. Exemplary arylene groups include optionally substituted phenylene, naphthylene and indanylene. When $Ar^2$ is arylene this may particularly represent an optionally substituted phenylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylsulfonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulfur, or nitrogen. Examples of azaheteroaryl groups include pyridyl, pyrimidinyl, quinolinyl, isoquinolinyl, quinazolinyl, imidazolyl, and benzimidazolyl.

"Azaheteroaryldiyl" means an optionally substituted bivalent radical derived from an azaheteroaryl group.

"Cyclic amine" means a 3 to 8 membered monocyclic cycloalkyl ring system where one of the ring carbon atoms is replaced by nitrogen and which (i) may optionally contain an additional heteroatom selected from O, S or $NY^6$ (where $Y^6$ is hydrogen, alkyl, arylalkyl, and aryl) and (ii) may be fused to additional aryl or heteroaryl ring to form a bicyclic ring system. Exemplary cyclic amines include pyrrolidine, piperidine, morpholine, piperazine, indoline and pyrindoline.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl- group in which the cycloalkenyl and alkyl moieties are as previously described. Exemplary cycloalkenylalkyl groups include cyclopentenylmethyl, cyclohexenylmethyl or cycloheptenylmethyl.

"Cycloalkenylene" means a bivalent radical derived from an unsaturated monocyclic hydrocarbon of about 3 to about 10 carbon atoms by removing a hydrogen atom from each of two different carbon atoms of the ring. Exemplary cycloalkenylene radicals include cyclopentenylene and cyclohexenylene.

"Cycloalkyl" means a saturated monocyclic or bicyclic ring system of about 3 to about 10 carbon atoms optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkenyl" means a cycloalkyl-alkenyl- group in which the cycloalkyl and alkenyl moieties are as previously described. Exemplary monocyclic cycloalkylalkenyl groups include cyclopentylvinylene and cyclohexylvinylene.

"Cycloalkylalkyl" means a cycloalkyl-alkyl- group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylalkynyl" means a cycloalkyl-alkynyl- group in which the cycloalkyl and alkynyl moieties are as previously described. Exemplary monocyclic cycloalkylalkynyl groups include cyclopropylethynyl, cyclopentylethynyl and cyclohexylethynyl.

"Cycloalkylene" means a bivalent radical derived from a saturated monocyclic hydrocarbon of about 3 to about 10 carbon atoms by removing a hydrogen atom from each of two different carbon atoms of the ring. Exemplary cycloalkenylene radicals include cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulfur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above.

"Heteroarylalkenyl" means a heteroaryl-alkenyl- group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl- group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl- group in which the heteroaryl and alkynyl moieties are as previously described. Exemplary heteroarylalkenyl groups include pyridylethynyl and 3-pyridylbut-2-ynyl.

"Heteroaryldiyl" means a bivalent radical derived from an aromatic monocyclic or multicyclic organic moiety of about 5 to about 10 ring members in which one or more of the ring members is/are element(s) other than carbon, for example nitrogen, oxygen or sulfur, and optionally substituted by one or more "aryl group substituents" as defined above. When $Ar^2$ is an optionally substituted heteroaryldiyl group this may particularly represent an optionally substituted "azaheteroaryldiyl" group.

"Heteroaryloxy" means an heteroaryl-O— group in which the heteroaryl group is as previously described. Exemplary heteroaryloxy groups include optionally substituted pyridyloxy.

"Heteroarylsulfonylcarbamoyl" means a heteroaryl-$SO_2$—NH—C(=O)— group in which the heteroaryl group is as previously described.

"Heterocycloalkyl" means: (i) a cycloalkyl group of about 3 to 7 ring members which contains one or more heteroatoms selected from O, S or $NY^6$ and which may optionally be substituted by oxo; (ii) an optionally substituted partially saturated multicyclic heterocarbocyclic moiety in which an aryl (or heteroaryl ring) and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Heterocycloalkylene" means a bivalent radical derived from a saturated monocyclic hydrocarbon of about 5 to about 7 atoms, which contains one or more heteroatoms selected from O, S or $NY^6$ and is optionally substituted by oxo, by removing a hydrogen atom from each of two different carbon atoms of the ring, or when $NY^6$ is NH by removing a hydrogen atom from one carbon atom of the ring and a hydrogen atom from the NH, or when the ring contains two $NY^6$ heteroatoms and $NY^6$ is NH by removing a hydrogen atom from both nitrogen atoms. When $L^1$ is a heterocycloalkylene group this may particularly represent a bivalent radical derived pyrrolidine, especially 3,4-pyrrolidinediyl.

"Prodrug" means a compound which is convertible in vivo by metabolic means (e.g., by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of formula (I) containing a carboxy group, are for example those described by F. J. Leinweber, Drug Metab. Res., 1987, 18, page 379.

Suitable esters of compounds of formula (I) containing both a carboxy group and a hydroxy group within the moiety —$L^1$—Y, include lactones, formed by loss of water between said carboxy and hydroxy groups. Examples of lactones include caprolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g., an alkylated nitrogen atom, more especially (morpholino-methyl)benzoates, e.g., 3- or 4-(morpholinomethyl)-benzoates, and (4-alkylpiperazin-1-yl)benzoates, e.g., 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g., hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates,p-toluenesulfonates, cyclohexylsulfamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent a group $R^3$—NH—$Ar^1$—$L^2$— in which: $L^2$ is a straight or branched $C_{1-6}$alkylene chain, more particularly a straight $C_{1-4}$alkylene chain such as methylene or ethylene, preferably methylene; $Ar^1$ is an 8 to 10 membered bicyclic system

in which (i) ring

is a 5 or 6 membered optionally substituted heterocycle, preferably a 5 membered heteroaryl ring, (ii) ring

is a 5 or 6 membered optionally substituted heterocycle or an optionally substituted benzene ring, preferably a benzene ring, (iii) each ring is optionally substituted by one or more "aryl group substituents" as defined above, (iv) the two rings are joined together by a carbon-carbon linkage or a carbon-nitrogen linkage, and

is preferably optionally substituted benzoxazolyl or optionally substituted benzimidazolyl, each [more particularly ring

] optionally substituted by one or more "aryl group substituents" as defined above [examples of particular aryl group substituents include $C_{1-4}$alkyl (e.g., methyl), $C_{1-4}$alkoxy (e.g., methoxy), amino, halogen, hydroxy, $C_{1-4}$alkylthio, $C_{1-4}$alkylsulfinyl, $C_{1-4}$alkylsulfonyl, nitro or trifluoromethyl]; and $R^3$ is optionally substituted aryl, such as a 2-substituted phenyl, [examples of particular aryl group substituents include $C_{1-4}$alkyl (e.g., methyl), $C_{1-4}$alkoxy (e.g., methoxy), halo (e.g., fluoro or chloro) and $Y^1Y^2N$— (e.g., dimethylamino)], and is preferably 2-methylphenyl.

$R^1$ may also particularly represent a group $R^3$—NH—C(=O)—NH—$Ar^2$—$L^2$— in which $L^2$ is a straight or branched $C_{1-6}$alkylene chain, more particularly a straight $C_{1-4}$alkylene chain such as methylene or ethylene, preferably methylene; $Ar^2$ is an optionally substituted phenylene, such as optionally substituted m- or p-phenylene, preferably optionally substituted p-phenylene, more preferably a 3-substituted p-phenylene, in which the substituent is ortho to the $R^3$—NH—C(=O)—NH— group, (preferred optional substituents include halo, $C_{1-4}$alkyl, $C_{1-4}$alkoxy, $C_{1-4}$alkylthio, $C_{1-4}$alkylsulfinyl and $C_{1-4}$alkylsulfonyl, especially chloro, methyl, ethyl, methoxy, methylthio, methylsulfinyl and methylsulfonyl), or $Ar^2$ is an optionally substituted heteroaryldiyl, such as optionally substituted azaheteroaryldiyl, (e.g., optionally substituted pyridinediyl, preferably a p-pyridinediyl), where the optional substituents include $C_{1-4}$alkyl and $C_{1-4}$alkoxy, especially methyl and methoxy, more preferably a pyridine-2,5-diyl, in which the $R^3$—NH—C(=O)—NH— group is adjacent to the pyridyl nitrogen atom, and which is substituted in the 4- or 6-position with a methyl or methoxy group; and $R^3$ is an optionally substituted aryl group (such as optionally substituted phenyl) or an optionally substituted heteroaryl (such as optionally substituted pyridyl), and is preferably 2- or 3-methyl(or methoxy)phenyl, more preferably 2-methylphenyl, or 3-methyl-2-pyridyl.

$R^2$ may particularly represent hydrogen.

$L^1$ may particularly represent an optionally substituted alkylene linkage especially optionally substituted ethylene or propylene, preferably optionally substituted ethylene. Preferred optional substituents include $C_{1-4}$alkyl, aryl, heteroaryl, —N($R^6$)—C(=O)—$R^4$, —N($R^6$)—C(=O)—O$R^4$, —N($R^6$)—SO$_2$—$R^4$, —N$Y^3Y^4$ and —[C(=O)—N($R^7$)—C($R^8$)($R^9$)]$_p$—C(=O)—N$Y^3Y^4$ or alkyl substituted by an acidic functional group, —C(=O)—N$Y^3Y^4$ or —N$Y^3Y^4$. In one preferred embodiment $L^1$ is a group

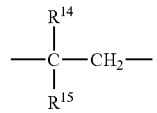

[ $R^{14}$ is hydrogen or $C_{1-4}$alkyl (e.g., methyl) and $R^{15}$ represents hydrogen or $C_{1-4}$alkyl, or where $R^{14}$ is hydrogen and $R^{15}$ represents aryl, heteroaryl, —N($R^6$)—C(=O)—$R^4$, —N($R^6$)—C(=O)—O$R^4$, —N($R^6$)—SO$_2$—$R^4$, —N$Y^3Y^4$ or —[C(=O)—N($R^7$)—C($R^8$)($R^9$)]$_p$—C(=O)—N$Y^3Y^4$, or alkyl substituted by an acidic functional group, —C(=O)—N$Y^3Y^4$ or —N$Y^3Y^4$], and is more preferably a group

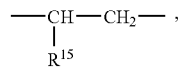

particularly

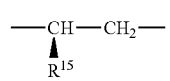

[where $R^{15}$ represents hydrogen, $C_{1-4}$alkyl, aryl, heteroaryl, —N($R^6$)—C(=O)—$R^4$, —N($R^6$)—C(=O)—O$R^4$, —N($R^6$)—SO$_2$—$R^4$ or —N$Y^3Y^4$ or alkyl substituted by carboxy, —OH, —OR$^{13}$ or —C(=O)—NY$^3$Y$^4$]. In another preferred embodiment L$^1$ is a group

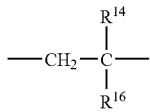

[where R$^{14}$ is hydrogen or C$_{1-4}$alkyl (e.g., methyl) and R$^{16}$ represents C$_{1-4}$alkyl, or where R$^{14}$ is hydrogen and R$^{16}$ represents aryl, heteroaryl, —N(R$^6$)—C(=O)—R$^4$, —N(R$^6$)—C(=O)—OR$^4$, —N(R$^6$)—SO$_2$—R$^4$, —NY$^3$Y$^4$ or —[C(=O)—N(R$^7$)—C(R$^8$)(R$^9$)]$_p$—C(=O)—NY$^3$Y$^4$, or alkyl substituted by an acidic functional group, —C(=O)—NY$^3$Y$^4$ or —NY$^3$Y$^4$], and is more preferably a group

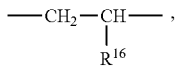

particularly

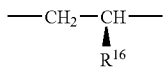

[where R$^{16}$ represents —N(R$^6$)—C(=O)—R$^4$, or —N(R$^6$)—SO$_2$—R$^4$].

Y may particularly represent carboxy.

It is to be understood that this invention covers all appropriate combinations of the particular and preferred groupings referred to herein.

A particular group of compounds of the invention are compounds of formula (Ia):

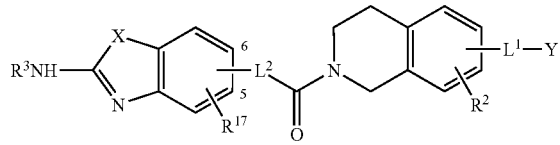

in which R$^2$, R$^3$, L$^1$, L$^2$ and Y are as hereinbefore defined, X is O or NR$^{18}$ (where R$^{18}$ is hydrogen or C$_{1-4}$alkyl), and R$^{17}$ is hydrogen or an aryl group substituent, and the corresponding N-oxides, and their prodrugs; and pharmaceutically acceptable salts and solvates (e.g., hydrates) of such compounds and their N-oxides and prodrugs.

Compounds of formula (Ia) in which R$^3$ represents optionally substituted aryl, especially 2-substituted phenyl, are preferred. Preferred optional substituents include C$_{1-4}$alkyl (e.g., methyl), C$_{1-4}$alkoxy (e.g., methoxy), halo (e.g., fluoro or chloro) and Y$^1$Y$^2$N— (e.g., dimethylamino). R$^3$ especially represents ortho-tolyl.

Compounds of formula (Ia) in which R$^{17}$ represents hydrogen, halo (e.g., chloro), C$_{1-4}$alkyl (e.g., methyl or ethyl) or C$_{1-4}$alkoxy (e.g., methoxy) are preferred.

Compounds of formula (Ia) in which L$^2$ represents a straight or branched C$_{1-6}$alkylene chain, especially a straight or branched C$_{1-4}$alkylene chain, more especially methylene, are preferred.

Compounds of formula (Ia) in which R$^2$ represents hydrogen are preferred.

Compounds of formula (Ia) in which L$^1$ represents an optionally substituted alkylene linkage, particularly optionally substituted ethylene or optionally substituted propylene, especially ethylene optionally substituted with C$_{1-4}$alkyl, aryl, heteroaryl, —N(R$^7$)—C(=O)—R$^8$, —N(R$^7$)—C(=O)—OR$^8$, —N(R$^7$)—SO$_2$—R$^8$, —NY$^1$Y$^2$ or —[C(=O)—N(R$^9$)—C(R$^5$)(R$^{10}$)]$_p$—C(=O)—NY$^1$Y$^2$, or alkyl substituted by an acidic functional group, —C(=O)—NY$^1$Y$^2$ or —NY$^1$Y$^2$, are preferred. In one preferred embodiment L$^1$ is a group

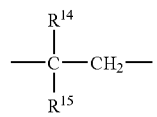

[where R$^{14}$ is hydrogen or C$_{1-4}$alkyl (e.g., methyl) and R$^{15}$ represents hydrogen or C$_{1-4}$alkyl, or where R$^{14}$ is hydrogen and R$^{15}$ represents aryl, heteroaryl, —N(R$^7$)—C(=O)—R$^8$, —N(R$^7$)—C(=O)—OR$^8$, —N(R$^7$)—SO$_2$—R$^8$, —NY$^1$Y$^2$ or —[C(=O)—N(R$^9$)—C(R$^5$)(R$^{10}$)]$_p$—C(=O)—NY$^1$Y$^2$, or alkyl substituted by an acidic functional group, —C(=O)—NY$^1$Y$^2$ or —NY$^1$Y$^2$], and is more preferably a group

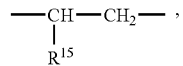

particularly

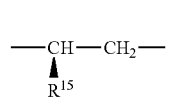

[where R$^{15}$ represents hydrogen, C$_{1-4}$alkyl, aryl, heteroaryl, —N(R$^7$)—C(=O)—R$^8$, —N(R$^7$)—C(=O)—OR$^8$, —N(R$^7$)—SO$_2$—R$^8$ or —Y$^1$Y$^2$ or alkyl substituted by carboxy, —OH, —OR$^{13}$ or —C(=O)—NY$^1$Y$^2$]. In another preferred embodiment L$^1$ is a group

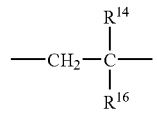

[where R$^{14}$ is hydrogen or C$_{1-4}$alkyl (e.g., methyl) and R$^{16}$ represents C$_{1-4}$alkyl, or where R$^{14}$ is hydrogen and R$^{16}$ represents aryl, heteroaryl, —N(R$^7$)—C(=O)—R$^8$, —N(R$^7$)—C(=O)—OR$^8$, —N(R$^7$)—SO$_2$—R$^8$, —NY$^1$Y$^2$ or —[C(=O)—N(R$^9$)—C(R$^5$)(R$^{10}$)]$_p$—C(=O)—NY$^1$Y$^2$, or alkyl substituted by an acidic functional group, —C(=O)—NY$^1$Y$^2$ or —NY$^1$Y$^2$], and is more preferably a group

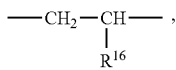

particularly

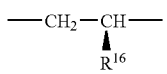

[where $R^{16}$ represents —N($R^6$)—C(=O)—$R^4$, or —N($R^6$)—SO$_2$—$R^4$].

Compounds of formula (Ia) in which Y represents carboxy are preferred.

The group

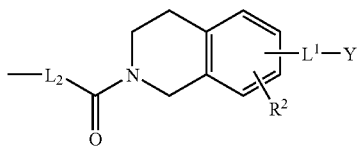

may preferably be attached at the ring 6 position or the ring 5 or 6 position when X is $NR^{18}$ and $R^{18}$ is $C_{1-4}$alkyl.

The group —$L^1$—Y may preferably be attached at position 6 or 7 of the tetrahydroisoquinoline ring.

A preferred group of compounds of the invention are compounds of formula (Ia) in which: $R^2$ is hydrogen; $R^3$ is optionally substituted aryl (especially ortho-tolyl); $R^{17}$ is hydrogen, chloro, methyl, ethyl or methoxy; $L^1$ is a

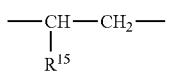

group particularly a

represents hydrogen, $C_{1-4}$alkyl, aryl, heteroaryl, —N($R^7$)—C(=O)—$R^8$, —N($R^7$)—C(=O)—O$R^8$, —N($R^7$)—SO$_2$—$R^8$ or —N$Y^1Y^2$, or alkyl substituted by carboxy, —OH, —$Z^1R^{13}$, —C(=O)—N$Y^1Y^2$ or —N$Y^1Y^2$; $L^2$ is a straight or branched $C_{1-4}$alkylene chain, especially methylene; X is O; Y is carboxy; the group

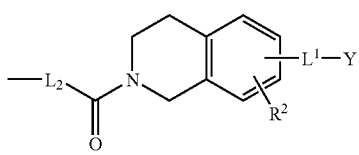

is attached at the ring 6 position; and the group —$L^1$—Y is attached at position 6 or 7 of the tetrahydroisoquinoline ring; and the corresponding N-oxides, and their prodrugs; and pharmaceutically acceptable salts and solvates (e.g., hydrates) of such compounds and their N-oxides and prodrugs.

Another preferred group of compounds of the invention are compounds of formula (Ia) in which: $R^2$ is hydrogen; $R^3$ is optionally substituted aryl (especially ortho-tolyl); $R^{17}$ is hydrogen, chloro, methyl, ethyl or methoxy; $L^1$ is a

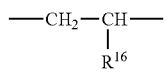

group, particularly

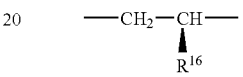

[where $R^{16}$ represents. —N($R^7$)—C(=O)—$R^8$, or —N($R^7$)—SO$_2$—$R^8$]; $L^2$ is a straight or branched $C_{1-4}$alkylene chain, especially methylene; X is O; Y is carboxy; the group

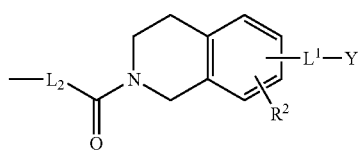

is attached at the ring 6 position; and the group —$L^1$—Y is attached at position 6 or 7 of the tetrahydroisoquinoline ring; and the corresponding N-oxides, and their prodrugs; and pharmaceutically acceptable salts and solvates (e.g., hydrates) of such compounds and their N-oxides and prodrugs.

Another preferred group of compounds of the invention are compounds of formula (Ia) in which: $R^2$ is hydrogen; $R^3$ is optionally substituted aryl (especially ortho-tolyl); $R^{17}$ is hydrogen, chloro, methyl, ethyl or methoxy; $L^1$ is a

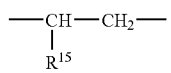

group particularly a

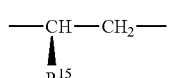

group, where $R^{15}$ represents hydrogen, $C_{1-4}$alkyl, aryl, heteroaryl, —N($R^7$)—C(=O)—$R^8$, —N($R^7$)—C(=O)—O$R^8$, —N($R^7$)—SO$_2$—$R^8$ or —N$Y^1Y^2$, or alkyl substituted by carboxy, —OH, —O$R^{13}$, —C(=O)—N$Y^1Y^2$ or —N$Y^1Y^2$; $L^4$ is a straight or branched $C_{1-4}$alkylene chain, (especially methylene); X is $NR^{18}$ (especially NH); Y is carboxy; the group

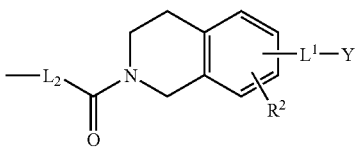

is attached at the ring 5 or 6 position; and the group —L$^1$—Y is attached at position 6 or 7 of the tetrahydroisoquinoline ring; and the corresponding N-oxides, and their prodrugs; and pharmaceutically acceptable salts and solvates (e.g., hydrates) of such compounds and their N-oxides and prodrugs.

Another preferred group of compounds of the invention are compounds of formula (Ia) in which: R$^2$ is hydrogen; R$^3$ is optionally substituted aryl (especially ortho-tolyl); R$^{17}$ is hydrogen, chloro, methyl, ethyl or methoxy; L$^1$ is a

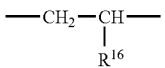

group, particularly

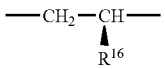

[where R$^{16}$ represents —N(R$^7$)—C(=O)—R$^8$, or —N(R$^7$)—SO$_2$—R$^8$]; L$^2$ is a straight or branched C$_{1-4}$alkylene chain, (especially methylene); X is NR$^{18}$ (especially NH); Y is carboxy; the group

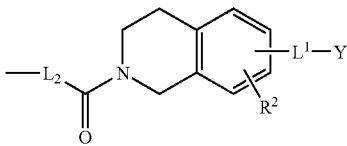

is attached at the ring 5 or 6 position; and the group —L$^1$—Y is attached at position 6 or 7 of the tetrahydroisoquinoline ring; and the corresponding N-oxides, and their prodrugs; and pharmaceutically acceptable salts and solvates (e.g., hydrates) of such compounds and their N-oxides and prodrugs.

Another particular group of compounds of the invention are compounds of formula (Ib):

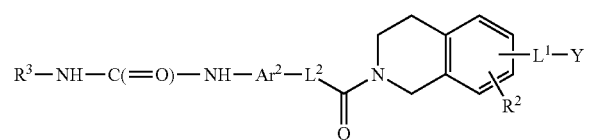

(Ib)

in which R$^2$, R$^3$, Ar$^2$, L$^1$, L$^2$ and Y are as hereinbefore defined, and the corresponding N-oxides, and their prodrugs; and pharmaceutically acceptable salts and solvates (e.g., hydrates) of such compounds and their N-oxides and prodrugs.

Compounds of formula (Ib) in which R$^3$ represents an optionally substituted aryl group, particularly an optionally substituted phenyl group, such as a 2-substituted phenyl, especially 2-methylphenyl, are preferred.

Compounds of formula (Ib) in which R$^3$ represents an optionally substituted heteroaryl group, particularly an optionally substituted pyridyl, such as optionally substituted 2-pyridyl, especially 3-methyl-2-pyridyl, are also preferred.

Compounds of formula (Ib) in which Ar$^2$ represents an optionally substituted phenylene, especially optionally substituted m- or p-phenylene, more especially optionally substituted p-phenylene, are preferred. Compounds of formula (Ib) in which Ar$^2$ represents 3-substituted p-phenylene, in which the substituent is ortho to the R$^3$—NH—C(=O)—NH— group, are particularly preferred. Preferred optional substituents include halo, C$_{1-4}$alkyl, C$_{1-4}$alkoxy, C$_{1-4}$alkylthio, C$_{1-4}$alkylsulfinyl and C$_{1-4}$alkylsulfonyl, especially chloro, methyl, ethyl, methoxy, methylthio, methylsulfinyl and methylsulfonyl.

Compounds of formula (Ib) in which Ar$^2$ is an optionally substituted heteroaryldiyl, such as optionally substituted pyridinediyl, particularly a p-pyridinediyl, more particularly a pyridine-2,5-diyl, in which the R$^3$—NH—C(=O)—NH— group is adjacent to the pyridyl nitrogen atom, and which is substituted in the 4- or 6-position, are also preferred. Preferred optional substituents include C$_{1-4}$alkyl and C$_{1-4}$alkoxy, especially methyl and methoxy.

Compounds of formula (Ib) in which L$^2$ represents a straight or branched C$_{1-6}$alkylene chain, more particularly a straight C$_{1-4}$alkylene chain such as methylene or ethylene, especially methylene, are preferred.

Compounds of formula (Ib) in which R$^2$ represents hydrogen are preferred.

Compounds of formula (Ib) in which L$^1$ represents an optionally substituted alkylene linkage, particularly optionally substituted ethylene or optionally substituted propylene, especially ethylene optionally substituted with C$_{1-4}$alkyl, aryl, heteroaryl, —N(R$^7$)—C(=O)—R$^8$, —N(R$^7$)—C(=O)—OR$^8$, —N(R$^7$)—SO$_2$—R$^8$, —NY$^1$Y$^2$ or —[C(=O)—N(R$^9$)—C(R$^5$)(R$^{10}$)]$_p$—C(=O)—NY$^1$Y$^2$, or alkyl substituted by an acidic functional group, —C(=O)—NY$^1$Y$^2$ or —NY$^1$Y$^2$, are preferred. In one preferred embodiment L$^1$ is a group

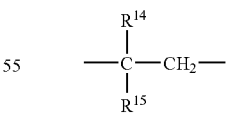

[where R$^{14}$ is hydrogen or C$_{1-4}$alkyl (e.g., methyl) and R$^{15}$ represents hydrogen or C$_{1-4}$alkyl, or where R$^{14}$ is hydrogen and R$^{15}$ represents aryl, heteroaryl, —N(R$^7$)—C(=O)—R$^8$, —N(R$^7$)—C(=O)—OR$^8$, —N(R$^7$)—SO$_2$—R$^8$, —NY$^1$Y$^2$ or —[C(=O)—N(R$^9$)—C(R$^5$)(R$^{10}$)]$_p$—C(=O)—NY$^1$Y$^2$, or alkyl substituted by an acidic functional group, —C(=O)—NY$^1$Y$^2$ or —NY$^1$Y$^2$], and is more preferably a group

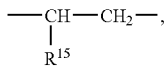

particularly

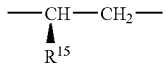

[where $R^{15}$ represents hydrogen, $C_{1-4}$alkyl, aryl, heteroaryl, —N($R^7$)—C(═O)—$R^8$, —N($R^7$)—C(═O)—$OR^8$, —N($R^7$)—$SO_2$—$R^8$ or —$NY^1Y^2$ or alkyl substituted by carboxy, —OH, —$OR^{13}$ or —C(═O)—$NY^1Y^2$]. In another preferred embodiment $L^1$ is a group

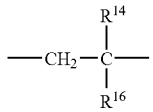

[where $R^{14}$ is hydrogen or $C_{1-4}$alkyl (e.g., methyl) and $R^{16}$ represents $C_{1-4}$alkyl, or where $R^{14}$ is hydrogen and $R^{16}$ represents aryl, heteroaryl, —N($R^7$)—C(═O)—$R^8$, —N($R^7$)—C(═O)—$OR^8$, —N($R^7$)—$SO_2$—$R^8$, —$NY^1Y^2$ or —[C(═O)—N($R^9$)—C($R^5$)($R^{10}$)]$_p$—C(═O)—$NY^1Y^2$, or alkyl substituted by an acidic functional group, —C(═O)—$NY^1Y^2$ or —$NY^1Y^2$], and is more preferably a group

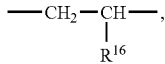

particularly

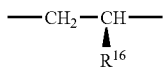

[where $R^{16}$ represents —N($R^7$)—C(═O)—$R^8$, or —N($R^7$)—$SO_2$—$R^8$].

Compounds of formula (Ib) in which Y represents carboxy are preferred.

A preferred group of compounds of the invention are compounds of formula (Ib) in which: $R^2$ is hydrogen; $R^3$ is a 2-substituted phenyl [especially 2-methyl(or methoxy) phenyl]; $Ar^2$ is optionally substituted m- or p-phenylene (especially 3-chloro-p-phenylene, 3-methyl-p-phenylene, 3-ethyl-p-phenylene, 3-methoxy-p-phenylene, 3-methylthio-p-phenylene, 3-methylsulfinyl-p-phenylene and 3-methylsulfonyl-p-phenylene) or optionally substituted p-pyridinediyl [especially 4(or 6)-methyl(or methoxy)-p-pyridine-2,5-diyl]; $L^1$ is a

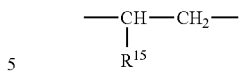

group particularly a

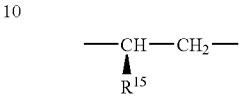

group, where $R^{15}$ represents hydrogen, $C_{1-4}$alkyl, aryl, heteroaryl, —N($R^7$)—C(═O)—$R^8$, —N($R^7$)—C(═O)—$OR^8$, —N($R^7$)—$SO_2$—$R^8$ or —$NY^1Y^2$, or alkyl substituted by carboxy, —OH, —$OR^{13}$, —C(═O)—$NY^1Y^2$; $L^2$ represents a straight or branched $C_{1-6}$alkylene chain, especially methylene; and Y represents carboxy; and the corresponding N-oxides, and their prodrugs; and pharmaceutically acceptable salts and solvates (e.g., hydrates) of such compounds and their N-oxides and prodrugs.

Another preferred group of compounds of the invention are compounds of formula (Ib) in which: $R^2$ is hydrogen; $R^3$ is a 2-substituted phenyl [especially 2-methyl(or methoxy) phenyl]; $Ar^2$ is optionally substituted m- or p-phenylene (especially 3-chloro-p-phenylene, 3-methyl-p-phenylene, 3-methoxy-p-phenylene, 3-methylthio-p-phenylene, 3-methylsulfinyl-p-phenylene and 3-methylsulfonyl-p-phenylene) or optionally substituted p-pyridinediyl [especially 4(or 6)-methyl(or methoxy)-p-pyridine-2,5-diyl]; $L^1$ is a

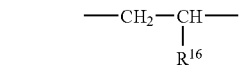

group, particularly

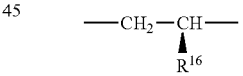

[where $R^{16}$ represents —N($R^7$)—C(═O)—$R^8$, or —N($R^7$)—$SO_2$—$R^8$]; $L^2$ represents a straight or branched $C_{1-6}$alkylene chain, especially methylene; and Y represents carboxy; and the corresponding N-oxides, and their prodrugs; and pharmaceutically acceptable salts and solvates (e.g., hydrates) of such compounds and their N-oxides and prodrugs.

Particular compounds of the invention are selected from the compounds formed by joining the acyl carbon atom (C*) of one of the fragments (A1 to A18) shown in Table 1 to the nitrogen atom (N*) of one of the tetrahydroisoquinoline fragments (B1 to B3) shown in Table 2, and joining the carbon atom (C*) of the phenyl ring in one of the tetrahydroisoquinoline fragments (B1 to B3) shown in Table 2 to the carbon atom (C*) of one of the acidic fragments (C1 to C28) depicted in Table 3.

TABLE 1
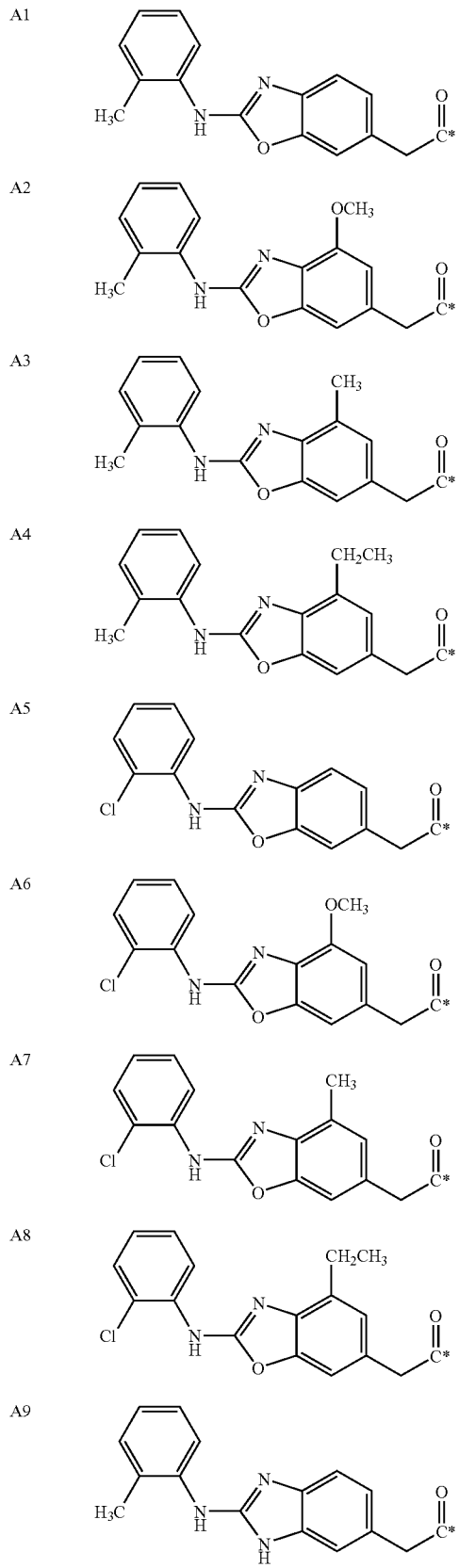
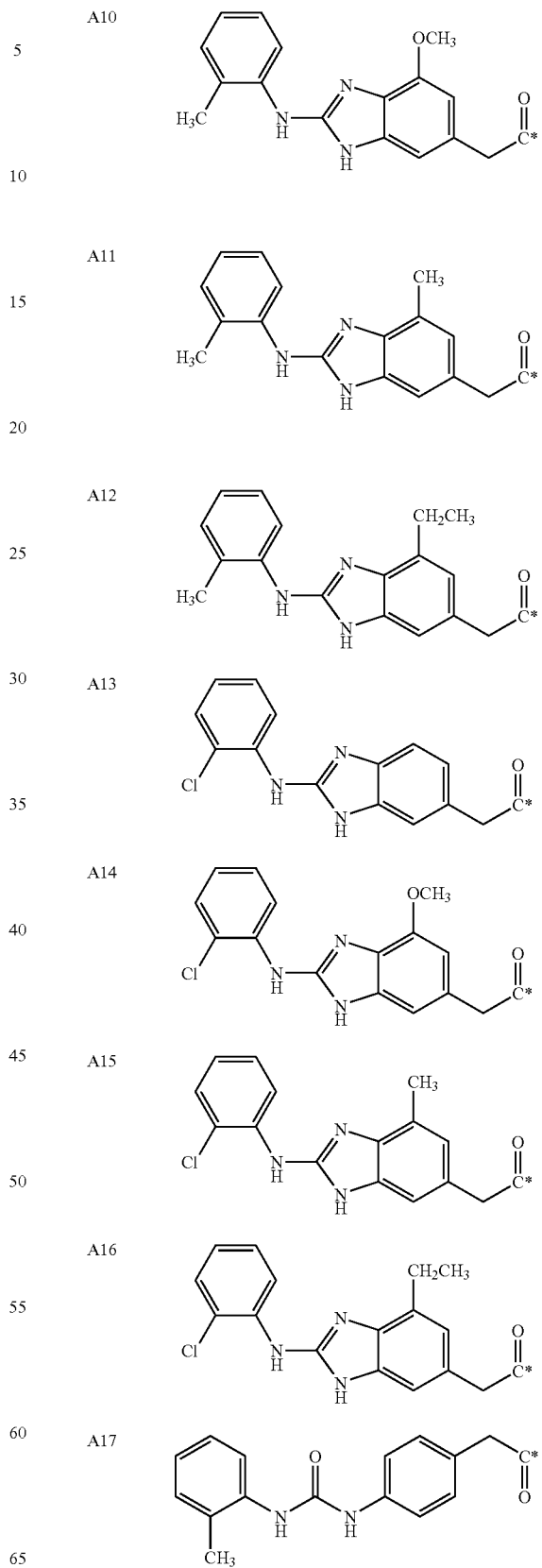

TABLE 1-continued

| | | |
|---|---|---|
| A18 | 2-methylphenyl-NH-C(=O)-NH-(3-methoxy-4-)phenyl-CH2-C*(=O) structure | |
| A19 | 2-methylphenyl-NH-(benzoxazol-2-yl), 6-C*(=O) structure | |
| A20 | 2,6-dichlorophenyl-C*(=O) structure | |

TABLE 2

| | |
|---|---|
| B1 | 1,2,3,4-tetrahydroisoquinoline, *N at 2, C* at 6 |
| B2 | 1,2,3,4-tetrahydroisoquinoline, *N at 2, C* at 7 |
| B3 | 5,6,7,8-tetrahydro-1,7-naphthyridine-like, *N and C* |

TABLE 3

| | |
|---|---|
| C1 | *CH(CH₃)—CH₂—CO₂H |
| C2 | *CH(CH₂CH₃)—CH₂—CO₂H |
| C3 | *CH(CH(CH₃)₂)—CH₂—CO₂H |
| C4 | *CH(CH₂CH(CH₃)₂)—CH₂—CO₂H |
| C5 | *CH(C(CH₃)₃)—CH₂—CO₂H |
| C6 | *CH(phenyl)—CH₂—CO₂H |
| C7 | *CH(4-fluorophenyl)—CH₂—CO₂H |
| C8 | *CH(pyridin-2-yl)—CH₂—CO₂H |
| C9 | *CH(pyridin-3-yl)—CH₂—CO₂H |
| C10 | *CH(pyridin-4-yl)—CH₂—CO₂H |
| C11 | *CH(furan-3-yl)—CH₂—CO₂H |
| C12 | *CH(furan-2-yl)—CH₂—CO₂H |
| C13 | *CH(thiophen-3-yl)—CH₂—CO₂H |
| C14 | *CH(thiophen-2-yl)—CH₂—CO₂H |
| C15 | *CH(piperidin-1-yl)—CH₂—CO₂H |

TABLE 3-continued

| | |
|---|---|
| C16 | 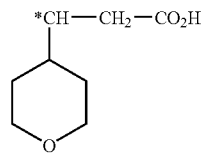 |
| C17 | 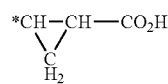 |
| C18 | 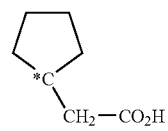 |
| C19 | 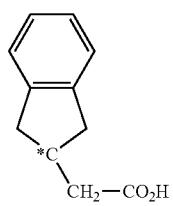 |
| C20 | *CH—CH₂—CO₂H<br>│<br>CH₂CO₂H |
| C21 | 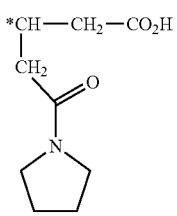 |
| C22 | *CH—CH₂—CO₂H<br>│<br>OMe |
| C23 | 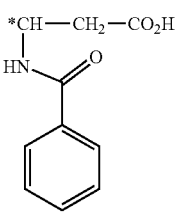 |
| C24 | 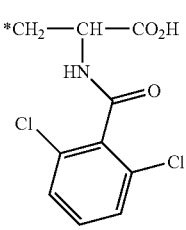 |

TABLE 3-continued

| | |
|---|---|
| C25 | 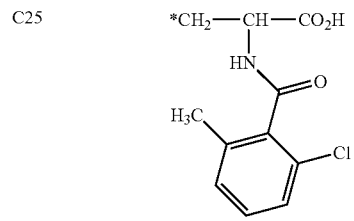 |
| C26 | 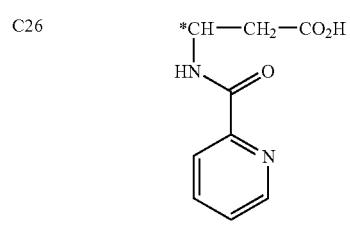 |
| C27 | 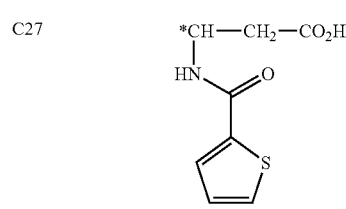 |
| C28 | 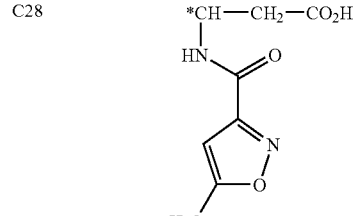 |
| C29 | 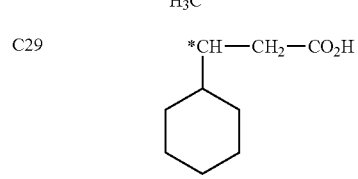 |
| C30 | *C═CH—CO₂H<br>│<br>CH₃ |

Compounds in accordance with the present invention may consist of any combination of the above-identified "A", "B", and "C" fragments.

Thus, for example, a compound denoted as A1-B1-C1 is the product of the combination of group A1 in Table 1 and B1 in Table 2 and C1 in Table 3, namely

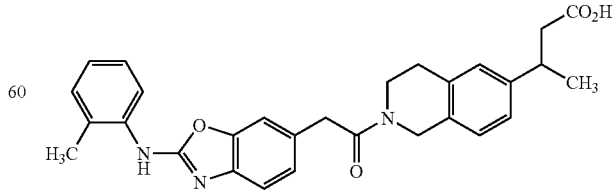

Particular compounds of the invention, as exemplified below, are selected from the following:

3-{((4-methyl-2-o-tolylamino-benzoxazol-6-yl)-acetyl)-1,2,3,4-tetrahydro-isoquinolin-6-yl}-butanonic acid, Example 1(a) [A3-B1-C1];
3-{((2-o-tolylamino-benzoxazol-6-yl)-acetyl)-1,2,3,4-tetrahydro-isoquinolin-7-yl}-butanoic acid, Example 1(b) [A1-B2-C1];
3-phenyl-3-{((2-o-tolylamino-benzoxazol-6-yl)-acetyl)-1,2,3,4-tetrahydro-isoquinolin-6-yl}-propanoic acid, Example 1(c) [A1-B1-C6];
3-cyclohexyl-3-{((2-o-tolylamino-benzoxazol-6-yl)-acetyl)-1,2,3,4-tetrahydro-isoquinolin-6-yl}-propanoic acid, Example 1(d) [A1-B1-C29];
3-(pyrid-4-yl)-3-{((2-o-tolylamino-benzoxazol-6-yl)-acetyl)-1,2,3,4-tetrahydro-isoquinolin-7-yl}-propanoic acid, Example 1(e) [A1-B2-C10];
3-{((2-o-tolylamino-benzoxazol-6-yl)-acetyl)-1,2,3,4-tetrahydro-isoquinolin-8-yl}-but-2-enoic acid, Example 1(f) [A1-B3-C30];
3-{((2-o-tolylamino-benzoxazol-6-yl)-acetyl-1,2,3,4-tetrahydro-isoquinolin-8-yl}-butanoic acid, Example 1(g) [A1-B3-C1];
3-{2-[(2-o-tolylamino-benzoxazol-6-yl)-carbonyl]-1,2,3,4-tetrahydro-isoquinolin-6-yl}-butanoic acid, Example 1(h) [A19-B1-C1];
{5-(3-methoxy-4-[3-(2-methylphenyl)ureido]-phenylacetylamino)-1,2,3,4-tetrahydro-isoquinolin-8-yl}-butanoic acid, Example 1(i) [A18-B3-C1];
2-(2,6-dichloro-benzoylamino)-3-[2-(2,6-dichloro-benzoyl]-1,2,3,4-tetrahydro-isoquinolin-7-yl]-propionic acid, Example 1(j) [A20-B2-C24];
3-phenyl-3-{((2-o-tolylamino-benzoxazol-6-yl)-acetyl)-1,2,3,4-tetrahydro-isoquinolin-7-yl}-propionic acid, Example 1(k) [A1-B2-C6];
3-{(2-o-tolylamino-benzoxazol-6-yl)-acetyl)-1,2,3,4-tetrahydro-isoquinolin-6-yl}-butanoic acid, Example 1(l) [A1-B1-C1];
3-(pyrid-4-yl)-3-{((2-o-tolylamino-benzoxazol-6-yl)-acetyl)-1,2,3,4-tetrahydro-isoquinolin-7-yl}-propanoic acid, enantiomer A, Example 1(m) [A1-B2-C10];
3-(pyrid-4-yl)-3-{((2-o-tolylamino-benzoxazol-6-yl)-acetyl)-1,2,3,4-tetrahydro-isoquinolin-7-yl}-propanoic acid, enantiomer B, Example 1(n) [A1-B2-C10];
and the corresponding N-oxides, and their prodrugs; and pharmaceutically acceptable salts and solvates (e.g., hydrates) of such compounds and their N-oxides and prodrugs.

Of these, preferred compounds of the invention include:
3-{((2-o-tolylamino-benzoxazol-6-yl)-acetyl)-1,2,3,4-tetrahydro-isoquinolin-7-yl}-butanoic acid, Example 1(b) [A1-B2-C1];
3-phenyl-3-{((2-o-tolylamino-benzoxazol-6-yl)-acetyl)-1,2,3,4-tetrahydro-isoquinolin-6-yl}-propanoic acid, Example 1(c) [A1-B1-C6];
3-(pyrid-4-yl)-3-{((2-o-tolylamino-benzoxazol-6-yl)-acetyl)-1,2,3,4-tetrahydro-isoquinolin-7-yl}-propanoic acid, Example 1(e) [A1-B2-C10];

and the corresponding N-oxides, and their prodrugs; and pharmaceutically acceptable salts and solvates (e.g., hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4\beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha 5\beta 1$ mediated cell adhesion. For example, compounds of the present invention are useful in the treatment of inflammatory diseases, for example joint inflammation including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds may be useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 ($\alpha 4\beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4\beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I), wherein $R^1$, $R^2$ and $L^1$ are as hereinbefore defined, and where Y is carboxy, may be prepared by hydrolysis of esters of formula (I), wherein $R^1$, $R^2$ and $L^1$ are as hereinbefore defined and Y is a —$CO_2R^{19}$ group (in which $R^{19}$ is alkyl, alkenyl or arylalkyl). The hydrolysis may conveniently be carried out by alkaline hydrolysis using a base, such as an alkali metal hydroxide, e.g., lithium hydroxide, or an alkali metal carbonate, e.g., potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I), wherein $R^1$, $R^2$ and $L^1$ are as hereinbefore defined, and where Y is carboxy, may be prepared by acid catalysed removal of the tert-butyl group of tert-butyl esters of formula (I), wherein $R^1$, $R^2$ and $L^1$ are as hereinbefore defined and Y is a —$CO_2R^{19}$ group (in which $R^{19}$ is tert-butyl), using standard reaction conditions, for example reaction with trifluoroacetic acid at a temperature at about room temperature.

As another example compounds of formula (I), wherein $R^1$, $R^2$ and $L^1$ are as hereinbefore defined, and where Y is carboxy, may be prepared by hydrogenation of compounds of formula (I) wherein $R^1$, $R^2$ and $L^1$ are as hereinbefore defined and Y is a —$CO_2R^{19}$ group (in which $R^{19}$ is arylmethyl, e.g., benzyl). The reaction may be carried out in the presence of ammonium formate and a suitable metal catalyst, e.g., palladium, supported on an inert carrier such as carbon, preferably in a solvent such as methanol or ethanol and at a temperature at about reflux temperature. The reaction may alternatively be carried out in the presence of a suitable metal catalyst, e.g., platinum or palladium optionally supported on an inert carrier such as carbon, preferably in a solvent such as methanol or ethanol. This reaction is most suitable for compounds of formula (I) where $L^1$ does not contain carbon-carbon multiple bonds.

In a process A compounds of formula (I), containing an amide bond may be prepared by coupling of an acid [or an acid halide (or anhydride)] with an amine to give an amide bond using standard peptide coupling procedures as described hereinafter.

As an example of process A, esters of formula (I), wherein $R^1$, $R^2$ and $L^1$ are as hereinbefore defined, and Y is a $—CO_2R^{19}$ group (in which $R^{19}$ is as hereinbefore defined), may be prepared by reacting a compound of formula (II):

wherein $R^{20}$ is optionally substituted aryl, optionally substituted heteroaryl, $R^3NH—Ar^1—L^2—$ or $R^3—NH—C(=O)—NH—Ar^2—L^2—$, and $X^1$ is a hydroxy group, a halogen atom, preferably chlorine, or $—O—C(=O)—R^{20}$ with an amine of formula (III):

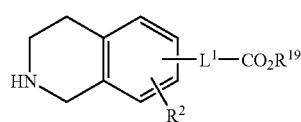

wherein $R^2$, $R^{19}$ and $L^1$ are as hereinbefore defined. When $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature. When $X^1$ is $—O—C(=O)—R^{20}$ the reaction may be carried out in an inert solvent, such as dichloromethane, optionally in the presence of a base, such as triethylamine, and at a temperature at about room temperature.

Esters of formula (I), wherein $R^1$ and $R^2$ are as hereinbefore defined, Y is a $—CO_2R^{19}$ group (in which $R^{19}$ is as hereinbefore defined) and $L^1$ contains a $—N(R^6)—C(=O)—R^4$ group (in which $R^4$ and $R^6$ are as hereinbefore defined) may be similarly prepared from the corresponding esters of formula (I) where $L^1$ contains a $—NHR^6$ group (in which $R^6$ is as hereinbefore defined) by reaction with a compound of formula $R^4—C(=O)—X^1$ wherein $R^4$ and $X^1$ are as hereinbefore defined.

Esters of formula (I), wherein $R^1$ and $R^2$ are as hereinbefore defined, Y is a $—CO_2R^{19}$ group (in which $R^{19}$ is as hereinbefore defined) and $L^1$ contains a $—N(R^6)—SO_2—R^4$ group (in which $R^4$ and $R^6$ are a hereinbefore defined), may be prepared from the corresponding esters of formula (I) where $L^1$ contains a $—NHR^6$ group (in which $R^6$ is as hereinbefore defined) by reaction with sulfonyl chlorides of formula $R^4—SO_2Cl$ wherein $R^4$ is as hereinbefore defined. The reaction is preferably carried out with the aid of a base, such as a tertiary amine, for example triethylamine, preferably in a solvent such as tetrahydrofuran and at a temperature from about 0° C. to about room temperature.

Esters of formula (I), wherein $R^1$ and $R^2$ are as hereinbefore defined, Y is a $—CO_2R^{19}$ group (in which $R^{19}$ is as hereinbefore defined) and $L^1$ contains a $—N(R^6)—C(=O)—OR^4$ group (in which $R^4$ and $R^6$ are as hereinbefore defined), may be prepared from the corresponding derivatives of formula (I) where $L^1$ contains a $—NHR^6$ group (in which $R^6$ is as hereinbefore defined) by reaction with compounds of formula $R^4O—C(=O)—X^1$ wherein $R^4$ and $X^1$ are as hereinbefore defined, in the presence of a suitable base, such as triethylamine or pyridine, and at a temperature from about 0° C. to about room temperature.

Esters of formula (I), wherein $R^1$ and $R^2$ are as hereinbefore defined, Y is a $—CO_2R^{19}$ group (in which $R^{19}$ is alkyl) and $L^1$ is

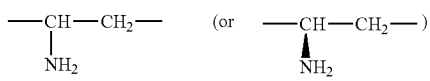

may be prepared by hydrogenation of the corresponding derivatives of formula (I), where $L^1$ is

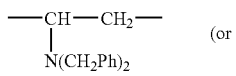

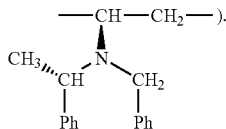

The reaction may be carried out in the presence of formic acid and a suitable metal catalyst, e.g., palladium, supported on an inert carrier such as carbon, at a temperature at about 60° C. The reaction may conveniently be carried out in the presence of a suitable metal catalyst, e.g., platinum or palladium optionally supported on an inert carrier such as carbon, preferably in a solvent such as methanol or ethanol.

Esters of formula (I), wherein $R^1$ and $R^2$ are as hereinbefore defined, Y is a $—CO_2R^{19}$ group (in which $R^{19}$ is as hereinbefore defined) and $L^1$ is a

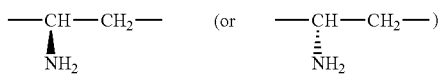

linkage, may also be obtained from the racemic mixture following standard recrystallisation of a suitable salt (for example recrystallisation of the tartrate salt), or by the application of standard enzymatic resolution procedures (for example those described by Soloshonok, V. A., et.al., Tetrahedron: Asymmetry 6 (1995) 7, 1601–1610).

Esters of formula (I), wherein $R^1$ and $R^2$ are as hereinbefore defined, Y is a $—CO_2R^{19}$ group (in which $R^{19}$ is as hereinbefore defined) and $L^1$ is a

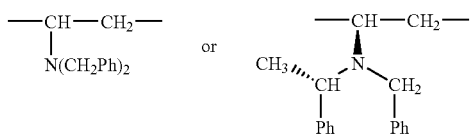

linkage, may be prepared by reacting an ester of formula (I), wherein $R^1$ and $R^2$ are as hereinbefore defined, Y is a $—CO_2R^{19}$ group (in which $R^{19}$ is as hereinbefore defined)

and L¹ is a —CH=CH— linkage, with an alkali metal hydride, such as sodium hydride, in an inert solvent, e.g., tetrahydrofuran, and at a temperature at about room temperature, and subsequent reaction with the anion derived from treating dibenzylamine, or (S)-N-benzyl-α-methylbenzylamine, with butyllithium, at a temperature at about −78° C.

Esters of formula (I), wherein R¹ and R² are as hereinbefore defined, Y is a —CO₂R¹⁹ group (in which R¹⁹ is as hereinbefore defined) and L¹ is alkenylene, alkynylene or cycloalkenylene in which the aliphatic carbon-carbon multiple bond is attached directly to the phenyl moiety in formula (I), may be prepared by coupling of compounds of formula (IV):

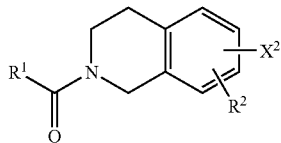

(IV)

wherein R¹ and R² are as hereinbefore defined and X² is a halogen, preferably bromine or iodine, atom with a compound of formula (V):

R²¹—CO₂R¹⁹     (V)

wherein R¹⁹ is as hereinbefore defined and R²¹ is alkenyl, alkynyl or cycloalkenyl. When X² is a bromine or iodine atom the reaction may be conveniently carried out in the presence of palladium acetate, a triarylphosphine, such as tri-o-tolylphosphine, and a tertiary amine, such as tributylamine, at a temperature up to about 110° C. This reaction is particularly suitable for the preparation of esters of formula (I) in which L¹ is vinylene. When X² is a chlorine atom the reaction may be conveniently carried out in the presence of sodium iodide, nickel bromide, palladium(0) bis(dibenzylideneacetone), a triarylphosphine, such as tri-o-tolylphosphine, and a tertiary amine, such as tributylamine, at a temperature up to about 110° C.

According to a further feature of the present invention, compounds of the invention may be prepared by interconversion of other compounds of the invention.

For example compounds of formula (I), wherein R¹, R² and L¹ are as hereinbefore defined and Y is a group —C(=O)—NHOH, may be prepared by reacting compounds of formula (I), wherein R¹, R² and L¹ are as hereinbefore defined and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl)hydroxylamine, O-(t-butyldimethylsilyl)-hydroxylamine, or O-(tetrahydropyranyl)hydroxylamine followed by treatment with acid.

As another example of the interconversion process, compounds of formula (I) containing sulfoxide linkages may be prepared by the oxidation of corresponding compounds containing —S— linkages. For example, the oxidation may conveniently be carried out by means of reaction with a peroxyacid, e.g., 3-chloroperbenzoic acid, preferably in an inert solvent, e.g., dichloromethane, preferably at or near room temperature, or alternatively by means of potassium hydrogen peroxomonosulfate in a medium such as aqueous methanol, buffered to about pH5, at temperatures between about 0° C. and room temperature. This latter method is preferred for compounds containing an acid-labile group.

As another example of the interconversion process, compounds of formula (I) containing sulfone linkages may be prepared by the oxidation of corresponding compounds containing —S— or sulfoxide linkages. For example, the oxidation may conveniently be carried out by means of reaction with a peroxyacid, e.g., 3-chloroperbenzoic acid, preferably in an inert solvent, e.g., dichloromethane, preferably at or near room temperature.

As another example of the interconversion process, compounds of formula (I), wherein R¹, R² and Y are as hereinbefore defined, and L¹ is optionally substituted alkylene, may be prepared by hydrogenation of the corresponding compounds of formula (I) in which L¹ is the corresponding optionally substituted alkenylene. The hydrogenation may be carried out using hydrogen (optionally under pressure) in the presence of a suitable metal catalyst, e.g., platinum or palladium optionally supported on an inert carrier such as carbon, preferably in a solvent such as methanol or ethanol, and at a temperature at about room temperature.

As another example of the interconversion process, compounds of formula (I) wherein R¹ and R² are as hereinbefore defined, L¹ is a

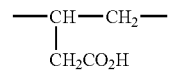

linkage and Y is carboxy, may be prepared by (i) reacting an ester of formula (I) wherein R¹ and R² are as hereinbefore defined, L¹ is a —CH=CH— linkage and Y is —CO₂R¹⁹ (in which R¹⁹ is as hereinbefore defined) with dimethyl malonate, in the presence of an alkali metal alkoxide, such as sodium methoxide, in methanol and at a temperature at about reflux temperature and (ii) treatment of the resulting compounds of formula (I) wherein R¹ and R² are as hereinbefore defined, L¹ is a

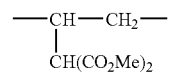

linkage and Y is —CO₂R¹⁹ with hydrochloric acid at reflux temperature.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g., acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g., aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g., hydrochloric acid.

Compounds of the present invention may be conveniently prepared, or formed during the process of the invention, as solvates (e.g., hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Compounds of formula (II) wherein $R^{20}$ is $R^3$—NH—C(=O)—NH—$Ar^2$—$L^2$— group (in which $R^3$, $Ar^2$ and $L^2$ are as hereinbefore defined) may be prepared by the application or adaptation of methods described in the specification of International Patent Application Publication No. WO 96/22966.

Acids of formula (II) wherein $R^{20}$ is $R^3$—NH—$Ar^1$—$L^2$— (in which $R^3$ and $L^4$ are as defined above, $Ar^1$ is

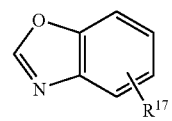

(in which $R^{17}$ is as hereinbefore defined) and $X^1$ is a hydroxy group may be prepared by reaction of compounds of formula (1):

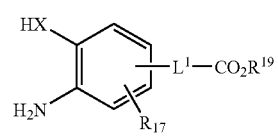

(1)

wherein $R^{17}$ and $L^1$ are as hereinbefore defined, $R^{16}$ is $C_{1-4}$alkyl and X is O, with isothiocyanates of formula $R^3$—N=S=O (in which $R^3$ is as hereinbefore defined) in ethanol and at room temperature, followed by reaction with a carbodiimide, such as dicyclohexylcarbodiimide or diisopropylcarbodiimide in ethanol and at a temperature from about room temperature to about reflux temperature, and subsequent hydrolysis using standard conditions, for example those described hereinbefore.

Acids of formula (II) wherein $R^{18}$ is $R^3$—NH—$Ar^1$—$L^2$— (in which $R^3$ and $L^2$ are as hereinbefore defined, $Ar^1$ is

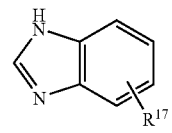

(in which R is as hereinbefore defined) and $X^1$ is hydroxy may be similarly prepared from compounds of formula (1) wherein $R^{17}$, $L^1$ and $R^{19}$ are as hereinbefore defined and X is NH.

Acid chlorides of formula (II) wherein $R^{20}$ is as hereinbefore defined and $X^1$ is a chlorine atom may be prepared from the corresponding acids of formula (II) wherein $R^{20}$ is as hereinbefore defined and $X^1$ is hydroxy, by the application of standard procedures for the conversion of acids to acid chlorides for example by reaction with oxalyl chloride.

Compounds of formula (III) wherein $R^2$, $R^{19}$ and $L^1$ are as defined hereinbefore, may be prepared by acid catalysed removal of the protecting group in compounds of formula (2):

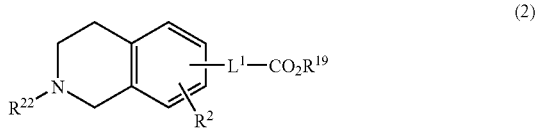

(2)

wherein $R^2$, $R^{19}$ and $L^1$ are as defined hereinbefore and $R^{22}$ is a suitable protecting group such as —COO$^t$Bu or —C(=O)—CF$_3$. When $R^{22}$ is —COO$^t$Bu the reaction may conveniently be carried out using trifluoroacetic acid in an inert solvent, such as dichloromethane, and at a temperature at about 0° C. When $R^{22}$ is —C(=O)—CF$_3$ the reaction may conveniently be carried out using a base such as sodium ethoxide in ethanol and at a temperature at about room temperature.

Compounds of formula (III) wherein $R^2$ is as defined hereinbefore, $R^{19}$ is alkyl and $L^1$ is alkylene or cycloalkylene may be prepared by hydrogenation of compounds of formula (2), wherein $R^2$ is as defined hereinbefore, $R^{19}$ is alkyl, $R^{22}$ is H [or a a protecting group (e.g., benzyl) that is conveniently removed during the hydrogenation] and $L^1$ is alkenylene, alkynylene or cycloalkenylene. The hydrogenation may be carried out using hydrogen (optionally under pressure) in the presence of a suitable catalyst, e.g., palladium hydroxide supported on an inert carrier such as carbon, in acetic acid and optionally in the presence of a co-solvent such as methanol or ethanol, and at a temperature at about room temperature.

Compounds of formula (III) wherein $R^2$ is as defined hereinbefore, $R^{19}$ is alkyl and $L^1$ is alkylene may be prepared by hydrogenation of isoquinolines of formula (3):

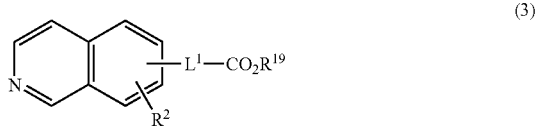

(3)

wherein $R^2$ is as defined hereinbefore, $R^{19}$ is alkyl and $L^1$ is alkenylene. The hydrogenation may be carried out using hydrogen (optionally under pressure) in the presence of a suitable catalyst, e.g., platinum oxide, in ethanol and in the presence of an acid such as hydrochloric acid, and at a temperature at about room temperature.

Compounds of formula (2) wherein $R^2$ is as defined hereinbefore, $R^{19}$ is alkyl, $R^{22}$ is a suitable protecting group, such as tertiary-butyloxycarbonyl, and $L^1$ is alkylene or cycloalkylene may be prepared by reduction compounds of formula (2) wherein $R^2$ is as defined hereinbefore, $R^{19}$ is alkyl, $R^{22}$ is a suitable protecting group, such as tertiary-butyloxycarbonyl, and $L^1$ is alkenylene, alkynylene or cycloalkenylene. The reduction may be carried out in the presence of ammonium formate and a suitable metal catalyst, e.g., palladium, supported on an inert carrier such as carbon, preferably in a solvent such as methanol or ethanol and at a temperature at about reflux temperature.

Compounds of formula (2) wherein $R^2$ is as defined hereinbefore, $R^{19}$ is alkyl, $R^{22}$ is a protecting group (e.g., benzyl or tertiary-butyloxycarbonyl) and $L^1$ is optionally substituted alkenylene, optionally substituted alkynylene or cycloalkenylene in which the carbon-carbon multiple bond is attached directly to the phenyl moiety in formula (2), may be prepared by reaction compounds of formula (4):

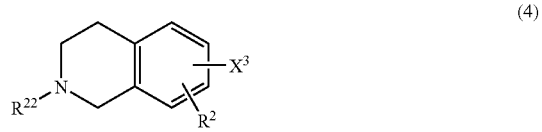

(4)

wherein $R^2$ and $R^{22}$ are as just defined and $X^3$ is an iodine, or preferably a bromine, atom, with a compound of formula (V) wherein $R^{19}$ and $R^{21}$ are as hereinbefore defined using standard Heck reaction conditions, for example reaction in the presence of palladium acetate, triphenylphosphine and tributylamine in an inert solvent, such as dimethylformamide, and at a temperature up to about 155° C.

Compounds of formula (3), wherein $R^2$ and $R^{19}$ are as defined hereinbefore and $L^1$ is optionally substituted alkenylene in which the carbon-carbon double bond is attached directly to the phenyl moiety in formula (3), may be similarly prepared from compounds of formula (5):

(5)

wherein $R^2$ and $X^3$ are as hereinbefore defined.

Compounds of formula (4) wherein $R^2$ is hydrogen, $X^3$ is as hereinbefore defined and $R^{22}$ is a suitable protecting group {e.g., CF$_3$C(=O)—} may be prepared by reaction of compounds of formula (6):

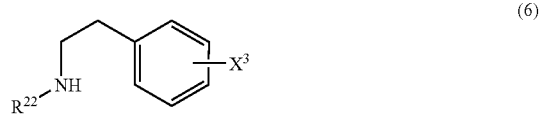

(6)

wherein $R^{22}$ and $X^3$ are as hereinbefore defined, with paraformaldehyde in the presence of acetic acid and sulphuric acid at a temperature at about room temperature.

Compounds of formula (6) wherein $R^{22}$ is CF$_3$C(=O)— and $X^3$ is as hereinbefore defined, may be prepared by reaction of the corresponding compounds of formula (6) in which $R^{22}$ is hydrogen with trifluoroacetic anhydride in the presence of a base, such as 2,6-lutidine, in an inert solvent, such as dichloromethane, and at room temperature.

Compounds of formula (6) wherein $R^{22}$ is hydrogen and $X^3$ is as hereinbefore defined, may be prepared by reduction of compounds of formula (7):

(7)

wherein $X^3$ is as hereinbefore defined. The reduction may conveniently be carried out with sodium borohydride in the presence of cobalt chloride, in an inert solvent, such as methanol, and at a temperature from about 0° C. to about 10° C.

Compounds of formula (III), (2) or (3) wherein $L^1$ is

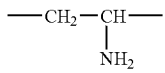

may be prepared by standard methodology for the preparation of ax-amino-acids for example those described in Organic Syntheses Based On Name Reactions and Unnamed Reactions, A. Hassner and C. Stumer, Pergamon, pages 275 and 374.

Compounds of formula (2) wherein $L^1$ is

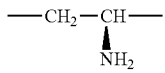

may be prepared by reaction of compounds of formula (8):

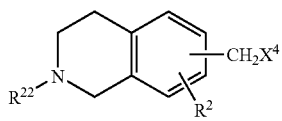

wherein $R^2$ and $R^{22}$ are as defined hereinbefore and $X^4$ is a bromine or chlorine atom with the anion derived from reaction of (2R)-(−)-2,5-dihydro-3,6-dimethoxy-2-isopropylpyrazine with butyllithium according to the method described by D. L. Boger and D. Yohannes, J. Org. Chem. [JOCEAH], 1990, 55, for the preparation of compound 31 on page 6010.

Compounds of formula (2) wherein $L^1$ is a

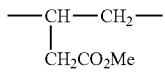

linkage, may be prepared by reacting compounds of formula (2) wherein $L^1$ is a —CH═CH— linkage, with dimethyl malonate, in the presence of an alkali metal alkoxide, such as sodium methoxide, in methanol and at a temperature at about reflux temperature.

The present invention is further Exemplified but not limited by the following illustrative Examples and Reference Examples.

High Pressure Liquid Chromatography/Mass Spectrometry (LC/MS) conditions for determination of retention times ($R_T$) were as follows: 3 micron Luna C18 (2) HPLC column (30 mm×4.6 mm) operated under gradient elution conditions with mixtures of (A) water containing 0.1% formic acid and (B) acetonitrile containing 0.1% formic acid as the mobile phase gradient : 0.00 minutes, 95% A:5% B; 0.50 minutes, 95% A:5% B; 4.50 minutes, 5% A:95% B; 5.00 minutes, 5% A:95% B; 5.50 minute 95% A:5% B; flow rate 2 ml/minute with approximately 200 μl/minute split to the Mass Spectrometer; injection volume 10–40 μl; in line Diode Array (220–450 nm), in line Evaporative light scattering (ELS) detection ELS—temperature 50° C., Gain 8–1.8 ml/minute; Source temperature 150° C.

EXAMPLE 1

(a) 3-{((4-Methyl-2-o-tolylamino-benzoxazol-6-yl)-acetyl)-1,2,3,4-tetrahydro-isoquinolin-6-yl}-butanoic acid A stirred solution of 3-{((4-methyl-2-o-tolylamino-benzoxazol-6-yl)-acetyl)-1,2,3,4-tetrahydro-isoquinolin -6-yl}-butanoic acid ethyl ester [0.1 g, Reference Example 1(a)] in ethanol (20 mL), under argon and at room temperature, was treated with sodium hydroxide solution (1 mL, 1M) and then heated at reflux temperature for 2.5 hours. The reaction mixture was evaporated to low volume (approximately 2 mL) and then treated with water (12 mL). This mixture was acidified to pH 1 by addition of hydrochloric acid (1.75 mL, 1M) and cooled in ice. The resulting solid was filtered, then washed three times with water (3 mL) and then dried at 60° C. under vacuum to give the title compound as a white solid. LC-MS: $R_T$=3.53 minutes; MS (ES)=498 (M+H)$^+$.

(b) By proceeding in a similar manner to Example 1(a) but using 3-{((2-o-tolylamino-benzoxazol-6-yl)-acetyl)-1,2,3,4-tetrahydro-isoquinolin-7-yl}-butanoic acid ethyl ester {Reference Example 1(b)} there was prepared 3-{((2-o-tolylamino-benzoxazol-6-yl)-acetyl)-1,2,3,4-tetrahydro-isoquinolin-7-yl}-butanoic acid as a white solid. LC-MS: $R_T$=3.36 minutes; MS (ES)=484 (M+H)$^+$.

(c) By proceeding in a similar manner to Example 1(a) but using 3-phenyl-3-{((2-o-tolylamino-benzoxazol-6-yl)-acetyl)-1,2,3,4-tetrahydro-isoquinolin-6-yl}-propanoic acid ethyl ester {Reference Example 1(c)} there was prepared 3-phenyl-3-{((2-o-tolylamino-benzoxazol-6-yl)-acetyl)-1,2,3,4-tetrahydro-isoquinolin-6-yl}-propanoic acid as a white solid. LC-MS: $R_T$=3.57 minutes; MS (ES)=546 (M+H)$^+$.

(d) By proceeding in a similar manner to Example 1(a) but using 3-cyclohexyl-3-{((2-o-tolylamino-benzoxazol-6-yl)-acetyl)-1,2,3,4-tetrahydro-isoquinolin-6-yl}-propanoic acid ethyl ester [Reference Example 1(d)} there was prepared 3-cyclohexyl-3-{((2-o-tolylamino-benzoxazol-6-yl)-acetyl)-1,2,3,4-tetrahydro-isoquinolin-6-yl}-propanoic acid as a white solid. LC-MS: $R_T$=3.98 minutes; MS (ES)=552 (M+H)$^+$.

(e) By proceeding in a similar manner to Example 1(a) but using a mixture of 3-(pyrid-4-yl)-3-{((2-o-tolylamino-benzoxazol-6-yl)-acetyl)-1,2,3,4-tetrahydro-isoquinolin-7-yl}-propanoic acid ethyl ester trifluoroacetate and 3-(pyrid-4-yl)-3-{((2-o-tolylamino-benzoxazol-6-yl)-acetyl)-1,2,3,4-tetrahydro-isoquinolin-7-yl}-propanoic acid methyl ester trifluoroacetate {Reference Example 1(e)} and subjecting the product to preparative HPLC under gradient elution conditions with mixtures of acetonitrile and water containing 0.1% trifluoroacetic acid (1:4 initially then a gradient of 1% acetonitrile/minute) there was prepared 3-(pyrid-4-yl)-3-{((2-o-tolylamino-benzoxazol-6-yl)-acetyl)-1,2,3,4-tetrahydro-isoquinolin-7-yl}-propanoic acid as a white solid. LC-MS: $R_T$=2.45 minutes; MS (ES)=547 (M+H)$^+$.

(f) By proceeding in a similar manner to Example 1(a) but using 3-{((2-o-tolylamino-benzoxazol-6-yl)-acetyl)-1,2,3,4-tetrahydro-isoquinolin-8-yl}-but-2-enoic acid ethyl ester {Reference Example 1(f)} there was prepared 3-{((2-o-tolylamino-benzoxazol-6-yl)-acetyl)-1,2,3,4-tetrahydro-isoquinolin-8-yl}-but-2-enoic acid as a white solid. LC-MS: $R_T$=3.38 minutes; MS (ES)=482 (M+H)$^+$.

(g) By proceeding in a similar manner to Example 1(a) but using 3-{((2-o-tolylamino-benzoxazol-6-yl)-acetyl)-1,2,3,4-tetrahydro-isoquinolin-8-yl}-butanoic acid ethyl ester {Reference Example 1(g)} and subjecting the product to preparative HPLC on a Hypersil Elite column (10 cm×2.1 cm) under gradient elution conditions with mixtures of acetonitrile and water containing 0.1% trifluoroacetic acid (3:10 initially then a gradient of 1% acetonitrile/minute) with a flow rate of 5 mL/minute there was prepared 3-{((2-o-tolylamino-benzoxazol-6-yl)-acetyl-1,2,3,4-tetrahydro-isoquinolin-8-yl}-butanoic acid as a white solid. LC-MS: $R_T$=3.42 minutes; MS (ES)=484 (M+H)$^+$.

(h) By proceeding in a similar manner to Example 1(a) but using 3-{2-[(2-o-tolylamino-benzoxazol-6-yl)-carbonyl]-1,2,3,4-tetrahydro-isoquinolin-6-yl}-butanoic acid ethyl ester {Reference Example 1(h)} there was prepared 3-{2-[(2-o-tolylamino-benzoxazol-6-yl)-carbonyl]-1,2,3,4-tetrahydro-isoquinolin-6-yl}-butanoic acid as a white solid. LC-MS: $R_T$=3.36 minutes; MS (ES)=470 (M+H)$^+$, 468 (M−H)$^-$.

(i) By proceeding in a similar manner to Example 1(a) but using {5-(3-methoxy-4-[3-(2-methylphenyl)ureido]phenylacetylamino)-1,2,3,4-tetrahydro-isoquinolin-8-yl}-butanoic acid ethyl ester {Reference Example 1(i)} there was prepared {5-(3-methoxy-4-[3-(2-methylphenyl)ureido]-phenylacetylamino)-1,2,3,4-tetrahydro-isoquinolin-8-yl}-butanoic acid as a white solid.

(j) By proceeding in a similar manner to Example 1(a) but using 2-(2,6-dichloro-benzoylamino)-3-[2-(2,6-dichloro-benzoyl]-1,2,3,4-tetrahydro-isoquinolin-7-yl]-propionic acid methyl ester (Reference Example 9) there was prepared 2-(2,6-dichloro-benzoylamino)-3-[2-(2,6-dichloro-benzoyl]-1,2,3,4-tetrahydro-isoquinolin-7-yl]-propionic acid as a pale yellow solid.

(k) By proceeding in a similar manner to Example 1(a) but using 3-phenyl-3-{((2-o-tolylamino-benzoxazol-6-yl)-acetyl)-1,2,3,4-tetrahydro-isoquinolin-7-yl}-propanoic acid ethyl ester {Reference Example 1(j)} there was prepared 3-phenyl-3-{((2-o-tolylamino-benzoxazol-6-yl)-acetyl)-1,2,3,4-tetrahydrotetrahydro-isoquinolin-7-yl}-propanoic acid as a white solid. LC-MS: $R_T$=3.62 minutes, MS (ES)=546 (M+H)$^+$, 544 (M−H)$^-$.

(l) By proceeding in a similar manner to Example 1(a) but using 3-{(2-o-tolylamino-benzoxazol-6-yl)-acetyl)-1,2,3,4-tetrahydro-isoquinolin-6-yl}-butanoic acid ethyl ester { Reference Example 1(k)} there was prepared 3-{(2-o-tolylamino-benzoxazol-6-yl)-acetyl)-1,2,3,4-tetrahydro-isoquinolin-6-yl}-butanoic acid as a white solid, m.p. softens from 100° C. and melts 123–140° C.

(m) By proceeding in a similar manner to Example 1(a) but using 3-(pyrid-4-yl)-3-{((2-o-tolylamino-benzoxazol-6-yl)-acetyl)-1,2,3,4-tetrahydro-isoquinolin-7-yl}-propanoic acid ethyl ester, enantiomer A {Reference Example 16(a)} there was prepared 3-(pyrid-4-yl)-3-{((2-o-tolylamino-benzoxazol-6-yl)-acetyl)-1,2,3,4-tetrahydro-isoquinolin-7-yl}-propanoic acid, enantiomer A. LC-MS:$R_T$=2.45 minutes, MS (ES)=547 (M+H)$^+$, 545 (M−H)$^-$.

(n) By proceeding in a similar manner to Example 1(a) but using 3-(pyrid-4-yl)-3-{((2-o-tolylamino-benzoxazol-6-yl)-acetyl)-1,2,3,4-tetrahydro-isoquinolin-7-yl}-propanoic acid ethyl ester, enantiomer B {Reference Example 16(b)} there was prepared 3-(pyrid-4-yl)-3-{((2-o-tolylamino-benzoxazol-6-yl)-acetyl)-1,2,3,4-tetrahydro-isoquinolin-7-yl}-propanoic acid, enantiomer B. LC-MS:$R_T$=2.45 minutes, MS (ES)=547 (M+H)$^+$, 545(M−H)$^-$.

REFERENCE EXAMPLE 1

(a) 3-{((4-Methyl-2-o-tolylamino-benzoxazol-6-yl)-acetyl)-1,2,3,4-tetrahydro-isoquinolin-6-yl}-butanoic acid ethyl ester A stirred solution of (4-methyl-2-(2-o-tolylamino)-benzoxazol-6-yl)-acetic acid (0.3 g, prepared according to the procedure described for Reference Example 9(b) in International Patent Application Publication No. WO 00/49005) in dry dimethylformamide (7.5 mL), under an argon atmosphere, was treated with O-(7-azabenzotriazol-1-yl)-1,1,3,3-tetramethyluronium hexafluorophosphate (0.7 g) then with di-isopropylethylamine (0.8 mL). After stirring at room temperature for 10 minutes the mixture was treated with a solution of ethyl 3-(1,2,3,4-tetrahydroisoquinolin-6-yl)-butanoate hydrochloride {0.38 g, Reference Example 2(a)} in dry dimethylformamide (7.5 mL) followed by di-isopropylethylamine (0.4 mL). The resulting dark solution was stirred at room temperature overnight then evaporated. The residual dark oil was treated with water (20 mL) and the mixture was acidified to pH 1 by addition of hydrochloric acid (5 mL, 1M) and then extracted with ethyl acetate (25 mL). The organic extract was washed with water (20 mL) then with brine (15 mL) then dried over magnesium sulfate and then evaporated. The residue was subjected to preparative HPLC on a Hypersil Elite column (10 cm×2.1 cm) under gradient elution conditions with mixtures of acetonitrile and water containing 0.1% trifluoroacetic acid (45:55 initially, rising at a rate of 1% acetonitrile/minute) with a flow rate of 5 mL/minute to give the title compound as an amber coloured glass. LC-MS: $R_T$=4.14 minutes; MS (ES) =526 (M+H)$^+$, MS (ES$^-$)=526 (M−H)$^-$.

(b) By proceeding in a similar manner to Reference Example 1(a) but using 2-o-tolylamino-benzoxazole-6-acetic acid (prepared according to the procedure described for Reference Example 4 in International Patent Application Publication No. WO 00/49005) and ethyl 3-(1,2,3,4-tetrahydro-isoquinolin-7-yl)-butanoate {Reference Example 4(a)} there was prepared 3-{((2-o-tolylamino-benzoxazol-6-yl)-acetyl)-1,2,3,4-tetrahydro-isoquinolin-7-yl}-butanoic acid ethyl ester as a clear oil. LC-MS: $R_T$=3.93 minutes; MS (ES)=512 (M+H)$^+$, MS (ES$^-$)=510 (M−H)$^-$.

(c) and (d) By proceeding in a similar manner to Reference Example 1(a) but using 2-o-tolylamino-benzoxazole-6-acetic acid and a mixture of 3-phenyl-3-(1,2,3,4-tetrahydroisoquinolin-6-yl)-propanoic acid ethyl ester hydrochloride and 3-cyclohexyl-3-(1,2,3,4-tetrahydroisoquinolin-6-yl)-propanoic acid ethyl ester hydrochloride {Reference Example 2(b)} and subjecting the product to preparative chromatography on a Hypersil Elite column (10 cm×2.1 cm) under gradient elution conditions with mixtures of acetonitrile and water containing 0.1% trifluoroacetic acid (50:50 initially, rising at a rate of 1% acetonitrile/minute) with a flow rate of 5 mL/minute there was prepared 3-phenyl-3-{((2-o-tolylamino-benzoxazol-6-yl)-acetyl)-1,2,3,4-tetrahydro-isoquinolin-6-yl}-propanoic acid ethyl ester, Reference Example 1(c), as a pale yellow gum {LC-MS: $R_T$=4.11 minutes; MS (ES)=574 (M+H)$^+$} and 3-cyclohexyl-3-{((2-o-tolylamino-benzoxazol-6-yl)-acetyl)-1,2,3,4-tetrahydro-isoquinolin-6-yl}-propanoic acid ethyl ester, Reference Example 1(d), as a pale yellow gum {LC-MS: $R_T$=4.61 minutes; MS (ES)=580 (M+H)$^+$}.

(e) By proceeding in a similar manner to Reference Example 1(a) but using 2-o-tolylaminobenzoxazole-6-acetic acid and a mixture of 3-(pyrid-4-yl)-3-(1,2,3,4-tetrahydro-isoquinolin-7-yl)-propanoic acid methyl ester and 3-(pyrid-4-yl)-3-(1,2,3,4-tetrahydro-isoquinolin-7-yl)-propanoic acid ethyl ester {Reference Example 4(b)} there was prepared a mixture of 3-(pyrid-4-yl)-3-{((2-o-tolylamino-benzoxazol-6-yl)-acetyl)-1,2,3,4-tetrahydro-isoquinolin-7-yl}-propanoic acid ethyl ester trifluoroacetate and 3-(pyrid-4-yl)-3-{((2-o-tolylamino-benzoxazol-6-yl)-acetyl)-1,2,3,4-tetrahydro-isoquinolin-7-yl}-propanoic acid methyl ester trifluoroacetate {Reference Example 1(e)}.

(f) and (g) By proceeding in a similar manner to Reference Example 1(a) but using 2-o-tolylaminobenzoxazole-6-acetic acid and a mixture of 3-(1,2,3,4-tetrahydroisoquinolin-8-yl)-but-2-enoic acid ethyl ester hydrochloride and 3-methyl-3-(1,2,3,4-tetrahydroisoquinolin-8-yl)-propanoic acid ethyl ester hydrochloride {Reference Example 2(c)} and subjecting the product to preparative chromatography on a Hypersil Elite column (10 cm×2.1 cm) under gradient elution conditions with mixtures of acetonitrile and water containing 0.1% trifluoroacetic acid (35:65 initially, rising at a rate of 1% acetonitrile/minute) with a flow rate of 5 mL/minute there was prepared 3-{((2-o-tolylamino-benzoxazol-6-yl)-acetyl)-1,2,3,4-tetrahydro-isoquinolin-8-yl}-but-2-enoic acid ethyl ester, Reference Example 1(f), {LC-MS: $R_T$=3.98 minutes; MS (ES)=510 (M+H)$^+$} and 3-{((2-o-tolylamino-benzoxazol-6-yl)-acetyl)-1,2,3,4-tetrahydro-isoquinolin-8-yl}-butanoic acid ethyl ester, Reference Example 1(g), {LC-MS: $R_T$=3.92 minutes; MS (ES)=512 (M+H)$^+$}.

(h) By proceeding in a similar manner to Reference Example 1(a) but using 2-o-tolylaminobenzoxazole-6-carboxylic acid there was prepared 3-{2-[(2-o-tolylamino-benzoxazol-6-yl)-carbonyl]-1,2,3,4-tetrahydro-isoquinolin-6-yl}-butanoic acid ethyl ester as a pale amber coloured glass. LC-MS: $R_T$=3.97 minutes; MS (ES)=498 (M+H)$^+$, 496 (M−H)$^-$.

(i) By proceeding in a similar manner to Reference Example 1(a) but using {5-(3-methoxy4-[3-(2-methylphenyl)ureido]phenylacetic acid (prepared as described in Example 21 of International Patent Application Publication No. WO 96/22966) there was prepared {5-(3-methoxy-4-[3-(2-methylphenyl)ureido]phenylacetyl amino)-1,2,3,4-tetrahydro-isoquinolin-8-yl}-butanoic acid ethyl ester as a fawn coloured glass. TLC: $R_F$=0.08 (silica plates, cyclohexane:ethylacetate, 1:1).

(j) By proceeding in a similar manner to Reference Example 1(a) but using 2-o-tolylaminobenzoxazole-6-acetic acid and 3-phenyl-3-(1,2,3,4-tetrahydroisoquinolin-7-yl)-propanoic acid ethyl ester {Reference Example 4(c)} there was prepared 3-phenyl-3-{((2-o-tolylamino-benzoxazol-6-yl)-acetyl)-1,2,3,4-tetrahydro-isoquinolin-7-yl}-propanoic acid ethyl ester as a pale yellow gum. LC-MS: $R_T$=4.17 minutes; MS (ES)=574 (M+H)$^+$, 572 (M−H)$^-$.

(k) By proceeding in a similar manner to Reference Example 1(a) but using 2-o-tolylaminobenzoxazole-6-acetic acid there was prepared 3-{(2-o-tolylamino-benzoxazol-6-yl)-acetyl)-1,2,3,4-tetrahydro-isoquinolin-6-yl}-butanoic acid ethyl ester as a clear gum.

REFERENCE EXAMPLE 2

(a) 3-(1,2,3,4-Tetrahydroisoquinolin-6-yl)-butanoic acid ethyl ester hydrochloride A solution of 3-(isoquinolin-6-yl)-but-2-enoic acid ethyl ester {0.5 g, Reference Example 3(a)} in ethanol (30 mL) was treated with concentrated hydrochloric acid (1.7 mL). This stirred solution was flushed with nitrogen then treated with platinum oxide (0.07 g) and then hydrogenated in the presence of hydrogen at 2 bar for 19 hours. The reaction mixture was filtered through Hyflo supercel and the filter pad was washed three times with ethanol (20 mL). The combined filtrate plus washings were evaporated to give the title compound as a pale green solid. MS (ES)=248 (M+H)$^+$.

(b) By proceeding in a similar manner to Reference Example 2(a) but using 3-(isoquinolin-6-yl)-3-phenyl-prop-2-enoic acid ethyl ester {Reference Example 3(b)} there was prepared a mixture of 3-phenyl-3-(1,2,3,4-tetrahydroisoquinolin-7-yl)-propanoic acid ethyl ester hydrochloride {LC-MS: $R_T$=2.36 minutes; MS (ES)=310 (M+H)$^+$} and ethyl 3-cyclohexyl-3-(1,2,3,4-tetrahydroisoquinolin-7-yl)-propanoate hydrochloride {LC-MS: $R_T$=2.73 minutes; MS (ES)=316 (M+H)$^+$} as an amber oil which was used without further purification.

(c) By proceeding in a similar manner to Reference Example 2(a) but using 3-(isoquinolin-8-yl)-but-2-enoic acid ethyl ester hydrochloride {Reference Example 3(c)} there was prepared a mixture of 3-(1,2,3,4-tetrahydroisoquinolin-8-yl)-but-2-enoic acid ethyl ester hydrochloride and 3-methyl-3-(1,2,3,4-tetrahydroisoquinolin-8-yl)-propanoic acid ethyl ester hydrochloride as a green glass.

REFERENCE EXAMPLE 3

(a) 3-(Isoquinolin-6-yl)-but-2-enoic acid ethyl ester

A stirred solution of 6-bromoisoquinoline (1.75 g) in dry dimethylformamide (15 mL), under argon, was treated with ethyl crotonate (1.7 mL) then with palladium (II) acetate (0.14 g), then with tri-(o-tolyl)phosphine (0.3 g) and then with tributylamine (8 mL). The suspension was stirred, under argon, at 140° C. for 3.5 hours, then stood at room temperature for 3 days and then evaporated. The residual dark oil was treated with ethyl acetate (50 mL) and the resulting solution was washed with water (30 mL) then twice with brine (25 mL), then dried over magnesium sulfate and then evaporated. The residue was subjected to flash chromatography on silica eluting initially with cyclohexane and then with a mixture of cyclohexane and ethyl acetate (9:1, v/v) to give the title compound as an amber coloured oil which solidified on cooling. MS (ES)=242 (M+H)$^+$.

(b) By proceeding in a similar manner to Reference Example 3(a) but using ethyl trans-cinnamate there was prepared 3-(isoquinolin-6-yl)-3-phenyl-prop-2-enoic acid ethyl ester as a viscous amber oil. MS (ES)=304 (M+H)$^+$.

(c) By proceeding in a similar manner to Reference Example 3(a) but using 8-bromoisoquinoline there was prepared 3-(isoquinolin-8-yl)-but-2-enoic acid ethyl ester hydrochloride. LC-MS: $R_T$=2.243 minutes; MS (ES)=242 (M+H)$^+$.

REFERENCE EXAMPLE 4

(a) 3-(1,2,3,4-Tetrahydroisoquinolin-7-yl)-butanoic acid ethyl ester

A stirred solution of 3-(2-trifluoroacetyl-1,2,3,4-tetrahydroisoquinolin-7-yl)-butanoic acid ethyl ester {0.5 g, Reference Example 5(a)} in ethanol (30 mL), under argon, was treated with sodium ethoxide (0.25 g). After stirring at room temperature for 1 hour the reaction mixture was evaporated. The residue was treated with ethyl acetate (30 mL) and the resulting solution was washed twice with saturated ammonium chloride solution (15 mL), then dried over magnesium sulfate and then evaporated to give the title compound as a yellow gum. MS (ES)=248 (M+H)$^+$.

(b) By proceeding in a similar manner to Reference Example 4(a) but using 3-(pyrid-4-yl)-3-(2-trifluoroacetyl-1,2,3,4-tetrahydroisoquinolin-7-yl)-propanoic acid methyl ester {Reference Example 5(b)}, methanol and sodium methoxide there was prepared a mixture of 3-(pyrid-4-yl)-3-(1,2,3,4-tetrahydro-isoquinolin-7-yl)-propanoic acid methyl ester and 3-(pyrid-4-yl)-3-(1,2,3,4-tetrahydro-isoquinolin-7-yl)-propanoic acid ethyl ester as a yellow oil which was used without further purification.

(c) By proceeding in a similar manner to Reference Example 4(a) but using 3-phenyl-3-(2-trifluoroacetyl-1,2,3,4-tetrahydroisoquinolin-7-yl)-propanoic acid ethyl ester {Reference Example 5(c)} there was prepared 3-phenyl-3-(1,2,3,4-tetrahydroisoquinolin-7-yl)-propanoic acid ethyl ester as a fawn coloured gum. LC-MS: $R_T$=2.21 minutes; MS (ES)=310 (M+H)$^+$.

REFERENCE EXAMPLE 5

(a) 3-(2-Trifluoroacetyl-1,2,3,4-tetrahydroisoquinolin-7-yl)-butanoic acid ethyl ester A mixture of 3-(2-trifluoroacetyl-1,2,3,4-tetrahydroisoquinolin-7-yl)-acrylic acid ethyl ester {1.5 g, Reference Example 6(a)}, industrial methylated spirits (80 mL) and palladium on carbon (0.15 g, 10%) was stirred under hydrogen for 18 hours. The reaction mixture was filtered through diatomaceous earth and the filter pad was washed with industrial methylated spirits. The combined filtrate and washings were evaporated to give the title compound as a colourless oil.

(b) By proceeding in a similar manner to Reference Example 5(a) but using 3-(pyrid-4-yl)-3-(2-trifluoroacetyl-1,2,3,4-tetrahydroisoquinolin-7-yl)-prop-2-enoic acid methyl ester {Reference Example 6(b)} there was prepared 3-(pyrid-4-yl)-3-(2-trifluoroacetyl-1,2,3,4-tetrahydroisoquinolin-7-yl)-propanoic acid methyl ester. LC-MS: $R_T$=2.33 minutes; MS (ES)=393 (M+H)$^+$.

(c) By proceeding in a similar manner to Reference Example 5(a) but using 3-phenyl-3-(2-trifluoroacetyl-1,2,3,4-tetrahydroisoquinolin-7-yl)-prop-2-enoic acid ethyl ester {Reference Example 6(c)} there was prepared 3-phenyl-3-(2-trifluoroacetyl-1,2,3,4-tetrahydroisoquinolin-7-yl)-propanoic acid ethyl ester as a yellow gum. LC-MS: $R_T$=4.20 minutes; MS (ES)=406 (M+H)$^+$, 428 (M+Na)$^+$.

REFERENCE EXAMPLE 6

(a) 3-(2-Trifluoroacetyl-1,2,3,4-tetrahydroisoquinolin-7-yl)-acrylic acid ethyl ester A solution of 7-bromo-2-trifluoroacetyl-1,2,3,4-tetrahydroisoquinoline (2.6 g, Reference Example 7), tri-o-tolylphosphine (0.37 g), palladium (II) acetate, ethyl acrylate (1.6 mL) and tributylamine (8.01 mL) in dry dimethylformamide (25 mL), under argon, was heated at 155° C. for 3 hours then stood at room temperature overnight. The reaction mixture was evaporated and the resulting black oil was partitioned between ethyl acetate (200 mL) and hydrochloric acid (200 mL, 2M). The organic phase was washed with hydrochloric acid (200 mL, 2M), then with water (100 mL), then with brine (100 mL), then dried over magnesium sulfate and then evaporated. The residual yellow oil was subjected to flash chromatography on silica under gradient elution conditions with a mixture of ethyl acetate and pentane (from 3:97 to 10:90, v/v) to give the title compound. LC-MS: $R_T$=4.05 minutes; no molecular ion observed.

(b) By proceeding in a similar manner to Reference Example 6(a) but using 3-(pyrid-4-yl)-prop-2-enoic acid methyl ester and subjecting the product to reverse phase chromatography on a Hypersil Elite C18 column (10 cm×2.1 cm) under gradient elution conditions with mixtures of acetonitrile and water containing 0.1% trifluoroacetic acid (25:75 initially, rising at a rate of 1% acetonitrile/minute) there was prepared 3-(pyrid4-yl)-3-(2-trifluoroacetyl-1,2,3,4-tetrahydroisoquinolin-7-yl)-prop-2-enoic acid methyl ester. LC-MS: $R_T$=2.63 minutes; MS (ES)=391 (M+H)$^+$.

(c) By proceeding in a similar manner to Reference Example 6(a) but using ethyl trans-cinnamate and subjecting the product to flash chromatography on silica eluting initially with cyclohexane and then with a mixture of cyclohexane and ethyl acetate (9:1, v/v) there was prepared 3-phenyl-3-(2-trifluoroacetyl-1,2,3,4-tetrahydroisoquinolin-7-yl)-prop-2-enoic acid ethyl ester as an amber oil which solidified on standing.

REFERENCE EXAMPLE 7

7-Bromo-2-trifluoroacetyl-1,2,3,4-tetrahydroisoquinoline

Concentrated sulfuric acid (35 mL) was added to glacial acetic acid (45mL) with stirring and ice-cooling. After stirring for 30 minutes the mixture was treated with N-2-(4-bromophenyl)ethyl trifluoroacetamide (10.4 g, Reference Example 8) and then with paraformaldehyde (1.75 g). This mixture was allowed to warm to room temperature and after stirring for a further 24 hours the pale brown solution was treated with a further aliquat of paraformaldehyde (0.8 g). After stirring for a further 24 hours the reaction mixture was treated with iced-water (500 mL) and then extracted three times with ethyl acetate (200 mL). The combined extracts were washed twice with water (200 mL), then four times with aqueous sodium bicarbonate solution (200 mL), then twice with water (200 mL), then dried over magnesium sulfate and then evaporated. The residual yellow oil was subjected to flash chromatography on silica eluting with a mixture of ethyl acetate and pentane (3:97, v/v) to give the title compound as a white crystalline solid. LC-MS: $R_T$=4.76 minutes; no molecular ion observed.

REFERENCE EXAMPLE 8

N-2-(4-Bromophenyl)ethyl trifluoroacetamide

A stirred solution of 2-(4-bromophenyl)ethylamine (7.9 g, prepared according to the procedure described by in J. Org. Chem., 1990, page 4530) and 2,6-lutidine (10.2 mL) in dry dichloromethane (150 mL), cooled in an ice-bath, was treated dropwise with trifluoroacetic anhydride (6.21 mL).

After stirring for 2 hours and standing at room temperature for 72 hours the reaction mixture was treated with water (100 mL) then stirred for a further 20 minutes. The organic phase was separated and then washed twice with hydrochloric acid (150 mL), then with water (100 mL), then with saturated aqueous sodium bicarbonate solution, then with water (100 mL), then dried over magnesium sulfate and then evaporated to give the title compound as a yellow solid. MS (ES) 294 and 296 (M−H)⁻.

REFERENCE EXAMPLE 9

(a) 2-(2,6-Dichloro-benzoylamino)-3-[2-(2,6-dichloro-benzoyl]-1,2,3,4-tetrahydro-isoquinolin-7-yl}-propionic acid methyl ester A stirred solution of 2-amino-3-[2-(2,6-dichloro-benzoyl]-1,2,3,4-tetrahydro-isoquinolin-7-yl]-propionic acid methyl ester (1.18 g, Reference Example 10) in dry pyridine (50 mL), under nitrogen and at room temperature, was treated dropwise with 2,6-dichloro-benzoyl chloride (0.67 g). The mixture was stirred at room temperature for 25 minutes and then at 65° C. for 40 minutes. The resulting dark red solution was cooled to room temperature and then evaporated. The residual red oil was dissolved in dichloromethane and this solution was washed with aqueous sodium bicarbonate solution (5%), then with water, then dried over magnesium sulfate and then evaporated. The residue was coated onto silica (8.5 g) using dichloromethane and then subjected to flash chromatography on silica eluting with a mixture of ethyl acetate and heptane (1:1, v/v) to give the title compound.

(b) By proceeding in a similar manner to Reference Example 9(a) but using 2-tert-butyloxycarbonylamino-1,2,3,4-tetrahydro-isoquinolin-7-yl]-propionic acid methyl ester {Reference Example 11(a)} there was prepared 2-tert-butyloxycarbonylamino-3-[2-(2,6-dichloro-benzoyl]-1,2,3,4-tetrahydro-isoquinolin-7-yl]-propionic acid methyl ester as a pale yellow solid.

REFERENCE EXAMPLE 10

2-Amino-3-[2-(2,6-dichloro-benzoyl]-1,2,3,4-tetrahydro-isoquinolin-7-yl]-propionic acid methyl ester A solution of 2-tert-butyloxycarbonylamino-3-[2-(2,6-dichloro-benzoyl]-1,2,3,4-tetrahydro-isoquinolin-7-yl]-propionic acid methyl ester {1.7 g, Reference Example 9(b)} in a mixture of trifluoroacetic acid (10 mL) and dichloromethane (30 mL), under nitrogen, was stirred at room temperature for 1.5 hours then evaporated. The residue was dissolved in dichloromethane and this solution was washed with aqueous sodium bicarbonate solution, then with water, then dried over magnesium sulfate and then evaporated to give the title compound (1.18 g) which was used without further purification.

REFERENCE EXAMPLE 11

(a) 2-tert-Butyloxycarbonylamino-1,2,3,4-tetrahydro-isoquinolin-7-yl]-propionic acid methyl ester A solution of 2-tert-butyloxycarbonylamino-3-[2-trifluoroacetyl)-1,2,3,4-tetrahydro-isoquinolin-7-yl]-propionic acid methyl ester (286 g, Reference Example 12) in metha-nol (120 mL) was treated with potassium carbonate solution (10 mL, 1%) at room temperature. After stirring for 1.5 hours the reaction mixture was treated with a further aliquot of potassium carbonate solution (10 mL, 1%), then a further aliquot (10 mL) after 2.5 hours and then a further aliquot (30 mL) after 5.5 hours. The reaction mixture was then stirred at room temperature overnight and then evaporated. The residue was treated with dichloromethane and water and the aqueous phase was extracted three times with dichloromethane. The combined organics were washed with water, then dried over magnesium sulfate and then evaporated to give the title compound (2.14 g).

(b) By proceeding in a similar manner to Reference Example 11(a) but using 3-(pyrid-4-yl)-3-(2-trifluoroacetyl-1,2,3,4-tetrahydroisoquinolin-7-yl)-propanoic acid methyl ester {Reference Example 5(b)} there was prepared 3-(pyrid-4-yl)-3-(1,2,3,4-tetrahydroisoquinolin-7-yl)-propanoic acid methyl ester as a yellow oil. LC-MS: $R_T$=0.64 minutes; MS (ES)=297 (M+H)⁺.

REFERENCE EXAMPLE 12

2-tert-Butyloxycarbonylamino-3-[2-trifluoroacetyl)-1,2,3,4-tetrahydro-isoquinolin-7-yl]-propionic acid methyl ester A solution of 2-tert-butyloxycarbonylamino-3-[2-trifluoroacetyl)-1,2,3,4-tetrahydro-isoquinolin-7-yl]-acrylic acid methyl ester (2.8 g, Reference Example 13) in industrial methylated spirits (200 mL), under nitrogen, was treated with palladium on carbon (0.38 g, 10%) and then hydrogen. After 2 hours an additional aliquot of palladium on carbon (0.4 g, 10%) was added to the reaction mixture and this mixture was stirred at room temperature overnight and then filtered through Celite. The filtrate was evaporated to give the title compound (2.86 g) as a colourless gum. LC-MS: 430 (M)⁺.

REFERENCE EXAMPLE 13

2-tert-Butyloxycarbonylamino-3-[2-trifluoroacetyl)-1,2,3,4-tetrahydro-isoquinolin-7-yl]-acrylic acid methyl ester A mixture of 7-bromo-[2-trifluoroacetyl)-1,2,3,4-tetrahydro-isoquinoline (4.29 g, Reference Example 7), N-(tert-butyloxycarbonyl)-dehydroalanine methyl ester (3.64 g, Reference Example 14), bis(tri-o-tolylphosphine)palladium (II) chloride 0.109 g), tri-o-tolylphosphine (0.212 g), triethylamine (7.7 mL) and dimethylformamide (100 mL), under nitrogen, was heated at 97° C. for 4 hours. then left at room temperature for 3 days and then evaporated. The residual red-orange syrup was partitioned between ethyl acetate and water. The organic phase was dried over sodium sulfate and evaporated. The residue was subjected to flash chromatography on silica eluting with a mixture of ethyl acetate and heptane (1:2, v/v) to give the title compound (2.9 g) as a yellow solid.

REFERENCE EXAMPLE 14

N-(tert-Butyloxycarbonyl)-dehydroalanine methyl ester

A solution of N-(tert-butyloxycarbonyl)-DL-serine methyl ester {5.48 g, Reference Example 15(a)} in tetrahydrofuran (60 mL) was treated with triethylamine (3.48 mL)

followed by carbonyldiimidazole (4.05 g). The mixture was stirred at room temperature overnight and then evaporated. The residue was extracted several times with tert-butyl methyl ether. The combined extracts were evaporated to give a colourless oil which was subjected to flash chromatography on silica eluting with toluene to give the title compound (3.64 g) as a colourless oil.

REFERENCE EXAMPLE 15

(a) N-(tert-Butyloxycarbonyl)-DL-serine methyl ester

A solution of DL-serine methyl ester hydrochloride (10 g) in dry dimethylformamide (100 mL) was treated with triethylamine (18 mL) followed by a solution of di-tert-butyl dicarbonate (14 g) in dry dimethylformamide (50 mL). After stirring at room temperature overnight the reaction mixture was evaporated. The residue was dissolved in ethyl acetate and this solution was washed twice with water and then evaporated. The resulting colourless oil (14 g) was dissolved in ethyl acetate and this solution was dried over sodium sulfate and then evaporated. The residue was subjected to flash chromatography on silica eluting with a mixture of ethyl acetate and heptane (2:3, v/v) to give the title compound (6.55 g) as a colourless oil.

(b) By proceeding in a similar manner to Reference Example 15(a) but using 3-(pyrid-4-yl)-3-(1,2,3,4-tetrahydroisoquinolin-7-yl)-propionic acid methyl ester {Reference Example 11(b)} and carrying out the reaction in tetrahydrofuran there was prepared 3-[2-(tert-butyloxycarbonylamino)-1,2,3,4-tetrahydro-isoquinolin-7-yl]-3-(pyrid-4-yl)-propionic acid methyl ester as a red oil. LC-MS: $R_T$=2.61 minutes, MS (ES)=397 (M+H)$^+$.

REFERENCE EXAMPLE 16

(a) 3-(Pyrid-4-yl)-3-{((2-o-tolylamino-benzoxazol-6-yl)-acetyl)-1,2,3,4-tetrahydro-isoquinolin-7-yl}-propanoic acid ethyl ester, enantiomer A A solution of 2-o-tolylaminobenzoxazole-6-acetic acid (0.124 g) and diisopropylethylamine (0.17 g) in dimethylformamide (2 mL) was treated with a solution of O-(7-azabenzotriazol-1-yl)-1,1,3,3-tetramethyluronium hexafluorophosphate (0.183 g) in dimethylformamide. After 10 minutes at room temperature this yellow solution was added dropwise to a rapidly stirred solution of 3-(1,2,3,4-tetrahydro-isoquinolin-7-yl)-3-(pyrid-4-yl)-propionic acid ethyl ester, enantiomer A {0.219 mmoles, Reference Example 17(a)} in dimethylformamide. After stirring at room temperature for 2.5 hours the reaction mixture was evaporated. The residual oil was dissolved in a mixture of acetonitrile, water and trifluoroacetic acid (25:75:0.1) and treated with dimethylformamide and trifluoroacetic acid to bring to pH2. This mixture was subjected to preparative HPLC {Hypersil Elite C18 column, 10 cm×2.1 cm, using a mixture of acetonitrile, water and trifluoroacetic acid (25:75:0.1) as the mobile phase followed by a 1% acetonitrile/minute gradient) to give the title compound. LC-MS:MS (ES)=575 (M+H)$^+$, 573 (M−H)$^-$.

(b) By proceeding in a similar manner to Reference Example 16(a) but using 3-(1,2,3,4-tetrahydro-isoquinolin-7-yl)-3-(pyrid-4-yl)-propionic acid ethyl ester, enantiomer B {Reference Example 17(b)} there was prepared 3-(pyrid-4-yl)-3-{((2-o-tolylamino-benzoxazol-6-yl)-acetyl)-1,2, 3,4-tetrahydro-isoquinolin-7-yl}-propanoic acid ethyl ester, enantiomer B. LC-MS:MS (ES)=575 (M+H)$^+$, 573 (M−H)$^-$.

REFERENCE EXAMPLE 17

(a) 3-(1,2,3,4-Tetrahydro-isoquinolin-7-yl)-3-(pyrid4-yl)-propionic acid ethyl ester, enantiomer A A solution of 3-(1,2,3,4-tetrahydro-isoquinolin-7-yl)-3-(pyrid-4-yl)-propionic acid, enantiomer A {Reference Example 18(a)} in ethanol (50 mL) was treated with concentrated hydrochloric acid (two drops) and then heated at reflux temperature, under nitrogen, for 8 hours. The pH of the reaction mixture was adjusted to ~5 by dropwise addition of sodium bicarbonate solution (5%) and this mixture was then evaporated to give the title compound which was used without further purification.

(b) By proceeding in a similar manner to Reference Example 17(a) but using 3-(1,2,3,4-tetrahydro-isoquinolin-7-yl)-3-(pyrid-4-yl)-propionic acid, enantiomer B {Reference Example 18(b)} there was prepared 3-(1,2,3,4-tetrahydro-isoquinolin-7-yl)-3-(pyrid-4-yl)-propionic acid ethyl ester, enantiomer B which was used without further purification.

REFERENCE EXAMPLE 18

3-(1,2,3,4-Tetrahydro-isoquinolin-7-yl)-3-(pyrid-4-yl)-propionic acid, enantiomer A A solution of 3-(1,2,3,4-tetrahydro-isoquinolin-7-yl)-3-(pyrid-4-yl)-propionic acid (S)-(−)-α-methylbenzyl amide, diastereoisomer A {0.092 g, Reference Example 19(a)} in hydrochloric acid 10 mL, 6N), under nitrogen, was heated at reflux temperature for 5 hours, then left at room temperature for 3 days, then heated at reflux temperature for 6.5 hours, then left at 100° overnight and then evaporated to give the title compound as a colourless solid. This material was used without further purification.

(b) By proceeding in a similar manner to Reference Example 16(a) but using 3-(1,2,3,4-tetrahydro-isoquinolin-7-yl)-3-(pyrid-4-yl)-propionic acid (S)-(−)-α-methylbenzyl amide, diastereoisomer B {Reference Example 19(b)} there was prepared 3-(1,2,3,4-tetrahydro-isoquinolin-7-yl)-3-(pyrid-4-yl)-propionoic acid ethyl ester, enantiomer B.

REFERENCE EXAMPLE 19

(a) 3-(1,2,3,4-Tetrahydro-isoquinolin-7-yl)-3-(pyrid-4-yl)-propionic acid (S)-(−)-α-methylbenzyl amide, diastereoisomer A, and (b) 3-(1,2,3,4-Tetrahydro-isoquinolin-7-yl)-3-(pyrid-4-yl)-propionic acid (S)-(−)-α-methylbenzyl amide, diastereoisomer B A solution of 3-[2-(tert-butyloxycarbonylamino)-1,2,3,4-tetrahydro-isoquinolin-7-yl]-3-(pyrid-4-yl)-propionic acid (0.6 g, Reference Example 20) in dry dimethylformamide (15 mL), under an argon atmosphere, was treated with di-isopropylethylamine (0.61 g) then with O-(7-azabenzotriazol-1-yl)-1,1,3,3-tetramethyluronium hexafluorophosphate (0.66 g). After stirring at room temperature for a few minutes the mixture was treated with (S)-(−)-α-methylbenzylamine (0.19 g) and stirring was continued at room temperature overnight. The reaction mixture was evaporated and the residue was partitioned, between dichloromethane and aqueous sodium carbonate solution (2%). The organic phase was washed with water and then evaporated. The residue (0.952 g) was subjected preparative reverse phase HPLC {Hypersil Elite C18 column, gradient elution using a mixture of 20% acetonitrile and 80% water containing 0.1% trifluoroacetic acid as the mobile phase with a 1% acetonitrile/minute gradient} followed by preparative HPLC {Dynamax silica column (30 cm×1.14 cm), 60 Å/81 µm, using a mixture of methanol, 1,2-dichloroethane, n-heptane and triethylamine (1:650:350:0.25) with a flow rate of 15 mL/minute} to give 3-(pyrid-4-yl)-3-{((2-o-tolylamino-benzoxazol-6-yl)-acetyl)-1,2,3,4-tetrahydro-isoquinolin-7-yl}-propanoic acid ethyl ester, diastereoisomer A {106 mg, Reference Example 19(a)} as the first to elute and 3-(pyrid-4-yl)-3-{((2-o-tolylamino-benzoxazol-6-yl)-acetyl)-1,2,3,4-tetrahydro-isoquinolin-7-yl}-propanoic acid ethyl ester, diastereoisomer B {92 mg, Reference Example 19(b)} as the second to elute.

REFERENCE EXAMPLE 20

3-[2-(tert-Butyloxycarbonylamino)-1,2,3,4-tetrahydro-isoquinolin-7-yl]-3-(pyrid-4-yl)-propionic acid A solution of 3-[2-(tert-butyloxycarbonylamino)-1,2,3,4-tetrahydro-isoquinolin-7-yl]-3-(pyrid-4-yl)-propionic acid methyl ester {1.46 g, Reference Example 15(b)} in ethanol (100 mL) was treated with sodium hydroxide solution (6 mL, 1N). This mixture was heated at 80° C. for 9 hours and then evaporated. The residue was partitioned between ethyl acetate and water which had been adjusted to pH 6 by addition of dilute hydrochloric acid. the aqueous phase was extracted twice with ethyl acetate and the combined organics were washed with water and then evaporated to give the title compound (0.6 g) which was used without further purification.

In Vitro and in Vivo Test Procedures

1. Inhibitory Effects of Compounds on VLA4 Dependent Cell Adhesion to Fibronectin and VCAM 1.1 Metabolic Labelling of RAMOS Cells.

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 µCi/100 mls of [$^3$H]-methionine (Amersham, UK) for 18 hours at 37° C.

1.2 96 Well Plate Preparation for Adhesion Assay.

Cytostar plates (Amersham, UK) were coated with 50 µl/well of either 3 µg/ml human soluble VCAM-1 (R&D Systems Ltd. UK) or 28.8 µg/ml human tissue Fibronectin (Sigma, UK). In control non-specific binding wells 50 µl phosphate buffered saline was added. The plates were then left to dry in an incubator at 25° C., overnight. The next day the plates were blocked with 200 µl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 µl/well of 3.6% dimethyl sulfoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 µl/well of the test compounds at the appropriate concentrations diluted in 3.6% dimethyl sulfoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 50 µl/well of cells in 3.6% dimethyl sulfoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis.

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for $IC_{50}$s for inhibition of cell adhesion to both fibronectin and VCAM-1. Particular compounds of the invention inhibit cell adhesion to fibronectin and VCAM-1 with $IC_{50}$'s in the range 100 micromolar to 77 nanomolar. Preferred compounds of the invention inhibit cell adhesion to fibronectin with $IC_{50}$'s below 100 nanomolar.

2. Inhibition of Antigen-induced Airway Inflammation in the Mouse and Rat 2.1 Sensitization of the Animals.

Rats (Brown Norway, Harland Olac, UK) are sensitized on days 0, 12 and 21 with ovalbumin (100 µg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 µg, i.p.) administered with aluminium hydroxide adjuvant (20 mg, i.p.) in saline (0.2 ml, i.p.).

2.2 Antigen Challenge.

Rats are challenged on any one day between days 28–38, while mice are challenged on any one day between days 20–30.

The animals are challenged by exposure for 30 minutes (rats) or 1 hour (mice) to an aerosol of ovalbumin (10 g/1) generated by an ultrasonic nebulizer (deVilbiss Ultraneb, US) and passed into an exposure chamber.

2.3 Treatment Protocols.

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t.

dosing). Dose volumes are: for rats 1 ml/kg, p.o. or 0.5 mg/kg, i.t.; for mice 10 ml/kg, p.o. or 1 ml/kg, i.t.

2.4 Assessment of Airway Inflammation.

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco. UK) containing 10% foetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK).

2.5 Data Analysis.

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where p<0.05, no statistical significance existed.

What is claimed is:

1. A compound of formula (I):

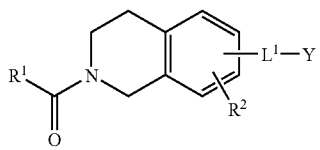

wherein:

R$^1$ represents R$^3$NH—Ar$^1$—L$^2$;
R$^2$ represents hydrogen, halogen, C$_{1-4}$alkyl or C$_{1-4}$alkoxy;
R$^3$ represents optionally substituted aryl;
R$^5$ represents alkyl, alkenyl, alkynyl, aryl, arylalkyl, arylalkenyl, arylalkynyl, cycloalkyl, cycloalkylalkyl, cycloalkylalkenyl, cycloalkylalkynyl, cycloalkenyl, cycloalkenylalkyl, heteroaryl, heteroarylalkyl, heteroarylalkenyl, heteroarylalkynyl, heterocycloalkyl or heterocycloalkylalkyl;

Ar$^1$ represents a fully unsaturated 8- to 10-membered bicyclic ring system containing at least one heteroatom selected from O, S or N, optionally substituted by one or more aryl group substituents;
L$^1$ represents R$^5$;
L$^2$ represents an alkylene chain;
Y is carboxy;

and the corresponding N-oxides and ester prodrugs thereof, and the pharmaceutically acceptable salts and solvates of such compounds, and the N-oxides and ester prodrugs thereof.

2. A compound according to claim 1 in which: L$^2$ is a straight or branched C$_{1-6}$alkylene chain; and Ar$^1$ is an 8- to 10-membered bicyclic system

in which (i) ring

is a 5- or 6-membered optionally substituted heterocycle, (ii) ring

is a 5- or 6-membered optionally substituted heterocycle or an optionally substituted benzene ring, and (iii) the two rings are joined together by a carbon-carbon linkage or a carbon-nitrogen linkage.

3. A compound according to claim 2 in which

is a 5-membered optionally substituted heterocycle, ring

is an optionally substituted benzene ring, and the two rings are joined together by a carbon-carbon linkage.

4. A compound according to claim 2 in which

is an optionally substituted benzoxazolyl or an optionally substituted benzimidazolyl, each in which the benzene ring contains the optional substituents.

5. A compound according to claim 2 in which ring

is a benzene ring optionally substituted by one of $C_{1-4}$ alkyl, $C_{1-4}$ alkoxy, amino, halogen, hydroxy, $C_{1-4}$ alkylthio, $C_{1-4}$ alkylsulfinyl, $C_{1-4}$ alkylsulfonyl, nitro or trifluoromethyl.

6. A compound according to claim 2 in which $R^3$ represents a 2-substituted phenyl.

7. A compound according to claim 6 in which $R^3$ represents 2-methylphenyl.

8. A compound according to claim 1 of formula (Ia):

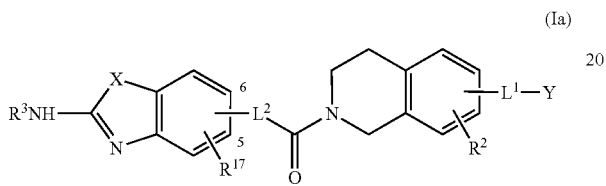

(Ia)

in which $R^2$, $R^3$, $L^1$, $L^2$ and Y are as defined in claim 1, X is O or $NR^{18}$, where $R^{18}$ is hydrogen or $C_{1-4}$alkyl, and $R^{17}$ is hydrogen or an aryl group substituent, and the corresponding N-oxides and ester prodrugs thereof, and the pharmaceutically acceptable salts and solvates of such compounds, and the N-oxides and ester prodrugs thereof.

9. A compound according to claim 8 in which $R^{17}$ represents hydrogen, halo, $C_{1-4}$ alkyl, or $C_{1-4}$alkoxy.

10. A compound according to claim 8 in which $L^2$ represents a straight or branched $C_{1-6}$alkylene chain.

11. A compound according to claim 8 in which the group

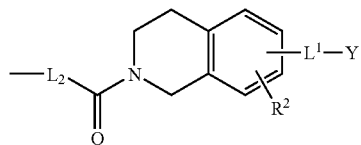

is attached at the ring 6 position or at the ring 5 or 6 position when X is $NR^{18}$ and $R^{18}$ is $C_{1-4}$alkyl.

12. A compound according to claim 8 in which the group $-L^1$-Y is attached at position 6 or 7 of the tetrahydroisoquinoline ring.

13. A compound according to claim 1 in which $L^1$ represents a $C_{1-4}$alkylene linkage optionally substituted by $C_{1-4}$alkyl, aryl, heteroaryl.

14. A compound according to claim 13 in which the $C_{1-4}$alkylene linkage is an ethylene linkage.

15. A compound according to claim 14 in which $L^1$ represents a group

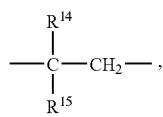

where $R^{14}$ is hydrogen or $C_{1-4}$alkyl and $R^{15}$ represents hydrogen or $C_{1-4}$alkyl; or where $R^{14}$ is hydrogen and $R^{15}$ represents aryl, heteroaryl.

16. A compound according to claim 14 in which $L^1$ represents a group

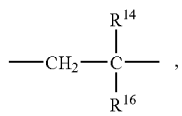

where $R^{14}$ is hydrogen or $C_{1-4}$alkyl and $R^{16}$ represents $C_{1-4}$alkyl; or where $R^{14}$ is hydrogen and $R^{16}$ represents aryl or, heteroaryl.

17. A compound according to claim 1 selected from:
3-{((4-methyl-2-o-tolylamino-benzoxazol-6-yl)-acetyl)-1,2,3,4-tetrahydro-isoquinolin-6-yl}-butanoic acid;
3-{((2-o-tolylamino-benzoxazol-6-yl)-acetyl)-1,2,3,4-tetrahydro-isoquinolin-7-yl}-butanoic acid;
3-phenyl-3-{((2-o-tolylamino-benzoxazol-6-yl)-acetyl)-1,2,3,4-tetrahydro-isoquinolin-6-yl}-propanoic acid;
3-cyclohexyl-3-{((2-o-tolylamino-benzoxazol-6-yl)-acetyl)-1,2,3,4-tetrahydro-isoquinolin-6-yl}-propanoic acid;
3-(pyrid-4-yl)-3-{((2-o-tolylamino-benzoxazol-6-yl)-acetyl)-1,2,3,4-tetrahydro-isoquinolin-7-yl}-propanoic acid;
3-{((2-o-tolylamino-benzoxazol-6-yl)-acetyl)-1,2,3,4-tetrahydro-isoquinolin-8-yl}-but-2-enoic acid;
3-{((2-o-tolylamino-benzoxazol-6-yl)-acetyl-1,2,3,4-tetrahydro-isoquinolin-8-yl}-butanoic acid; acid;
3-phenyl-3-{((2-o-tolylamino-benzoxazol-6-yl)-acetyl)-1,2,3,4-tetrahydro-isoquinolin-7-yl}-propanoic acid;
3-{(2-o-tolylamino-benzoxazol-6-yl)-acetyl)-1,2,3,4-tetrahydro-isoquinolin-6-yl}-butanoic acid;
3-(pyrid-4-yl)-3-{((2-o-tolylamino-benzoxazol-6-yl)-acetyl)-1,2,3,4-tetrahydro-isoquinolin-7-yl}-propanoic acid, enantiomer A;
3-(pyrid-4-yl)-3-{((2-o-tolylamino-benzoxazol-6-yl)-acetyl)-1,2,3,4-tetrahydro-isoquinolin-7-yl}-propanoic acid, enantiomer B;

and the corresponding N-oxides and ester prodrugs thereof, and the pharmaceutically acceptable salts and solvates of such compounds, and the N-oxides and ester prodrugs thereof.

18. A pharmaceutical composition comprising an effective amount of a compound according to claim 1 or a corresponding N-oxide or ester prodrug thereof, or a pharmaceutically acceptable salt or solvate of such a compound, or an N-oxide or ester prodrug thereof, in association with a pharmaceutically acceptable carrier or excipient.

19. A method for the treatment of a patient suffering from, or subject to, asthma comprising administering to said patient an effective amount of a compound according to claim 1 or a corresponding N-oxide or ester prodrug thereof, or a pharmaceutically acceptable salt or solvate of such a compound, or an N-oxide or ester prodrug thereof.

20. A method for the treatment of a patient suffering from, or subject to, an inflammatory bowel disease or a joint inflammation comprising administering to said patient an effective amount of a compound according to claim 1 or a corresponding N-oxide or ester prodrug thereof, or a phar maceutically acceptable salt or solvate of such a compound, or an N-oxide or ester prodrug thereof.

21. A method for the treatment of a patient suffering from, or subject to, asthma comprising administering to said patient an effective amount of a composition according to claim 18.

22. A method for the treatment of a patient suffering from, or subject to, an inflammatory bowel disease or a joint inflammation comprising administering to said patient an effective amount of a composition according to claim 18.

* * * * *